United States Patent
Madan et al.

(10) Patent No.: US 10,068,672 B2
(45) Date of Patent: Sep. 4, 2018

(54) METHOD FOR MODELING BEHAVIOR AND HEALTH CHANGES

(71) Applicant: Ginger.io, Inc., San Francisco, CA (US)

(72) Inventors: Anmol Madan, San Francico, CA (US); Sai Thejasvee Moturu, San Francisco, CA (US)

(73) Assignee: Ginger.io, Inc., San Francisco, CA (US)

( * ) Notice: Subject to any disclaimer, the term of this patent is extended or adjusted under 35 U.S.C. 154(b) by 0 days.

(21) Appl. No.: 15/798,005

(22) Filed: Oct. 30, 2017

(65) Prior Publication Data
US 2018/0052974 A1    Feb. 22, 2018

Related U.S. Application Data

(63) Continuation of application No. 13/969,349, filed on Aug. 16, 2013, now Pat. No. 9,836,581.

(60) Provisional application No. 61/683,867, filed on Aug. 16, 2012, provisional application No. 61/683,869, filed on Aug. 16, 2012.

(51) Int. Cl.
*G06F 19/00* (2018.01)
*G16H 50/50* (2018.01)
*G16H 10/20* (2018.01)

(52) U.S. Cl.
CPC ......... *G16H 50/50* (2018.01); *G06F 19/3418* (2013.01); *G06F 19/3437* (2013.01); *G06F 19/3456* (2013.01); *G06F 19/363* (2013.01); *G16H 10/20* (2018.01)

(58) Field of Classification Search
None
See application file for complete search history.

(56) References Cited

U.S. PATENT DOCUMENTS

| | | |
|---|---|---|
| 7,188,151 B2 | 3/2007 | Kumar et al. |
| 7,248,677 B2 | 7/2007 | Randall et al. |
| 7,584,166 B2 | 9/2009 | Grichnik |
| 7,761,309 B2 | 7/2010 | Sacco et al. |
| 8,160,901 B2 | 4/2012 | Heywood et al. |

(Continued)

FOREIGN PATENT DOCUMENTS

| | | |
|---|---|---|
| CN | 101600008 | 12/2009 |
| WO | 085308 | 7/2008 |

(Continued)

*Primary Examiner* — Michael Tomaszewski
(74) *Attorney, Agent, or Firm* — Jeffrey Schox; Brian Lao

(57) ABSTRACT

One method for supporting a patient through a treatment regimen includes: accessing a log of use of a native communication application executing on a mobile computing device by a patient; selecting a subgroup of a patient population based on the log of use of the native communication application and a communication behavior common to the subgroup; retrieving a regimen adherence model associated with the subgroup, the regimen adherence model defining a correlation between treatment regimen adherence and communication behavior for patients within the subgroup; predicting patient adherence to the treatment regimen based on the log of use of the native communication application and the regimen adherence model; and presenting a treatment-related notification based on the patient adherence through the mobile computing device.

24 Claims, 10 Drawing Sheets

(56) References Cited

U.S. PATENT DOCUMENTS

| | | |
|---|---|---|
| 8,500,635 B2 | 8/2013 | Zilca et al. |
| 2004/0225340 A1 | 11/2004 | Evans |
| 2005/0108051 A1 | 5/2005 | Weinstein |
| 2007/0094048 A1* | 4/2007 | Grichnik ............... G06Q 50/22 705/2 |
| 2007/0226012 A1 | 9/2007 | Salgado et al. |
| 2007/0288266 A1 | 12/2007 | Sysko et al. |
| 2010/0082367 A1* | 4/2010 | Hains ............... G06F 19/3456 705/2 |
| 2010/0203876 A1 | 8/2010 | Krishnaswamy |
| 2011/0009715 A1 | 1/2011 | O'Reilly et al. |
| 2011/0184250 A1 | 7/2011 | Schmidt et al. |
| 2013/0117040 A1 | 5/2013 | James et al. |
| 2013/0297536 A1* | 11/2013 | Almosni ............... G16H 50/20 706/12 |
| 2014/0039914 A1 | 2/2014 | Dansereau et al. |

FOREIGN PATENT DOCUMENTS

| | | |
|---|---|---|
| WO | 096634 | 8/2008 |
| WO | 025622 | 3/2012 |
| WO | 003247 | 1/2015 |

\* cited by examiner

METHOD FOR MODELING BEHAVIOR AND HEALTH CHANGES

CROSS-REFERENCE TO RELATED APPLICATIONS

This application is a continuation of U.S. patent application Ser. No. 13/969,349, filed 16 Aug. 2013, which claims the benefit of U.S. Provisional Application No. 61/683,867, filed 16 Aug. 2012, and U.S. Provisional Application No. 61/683,869, filed 16 Aug. 2012, which are all incorporated in their entireties herein by this reference.

TECHNICAL FIELD

This invention relates generally to the field of patient health and more specifically to a new and useful method for modeling behavior and health changes in the field of patient health.

DESCRIPTION OF THE EMBODIMENTS

The following description of the embodiments of the invention is not intended to limit the invention to these embodiments, but rather to enable any person skilled in the art to make and use this invention.

1. Methods

Figure 1A:
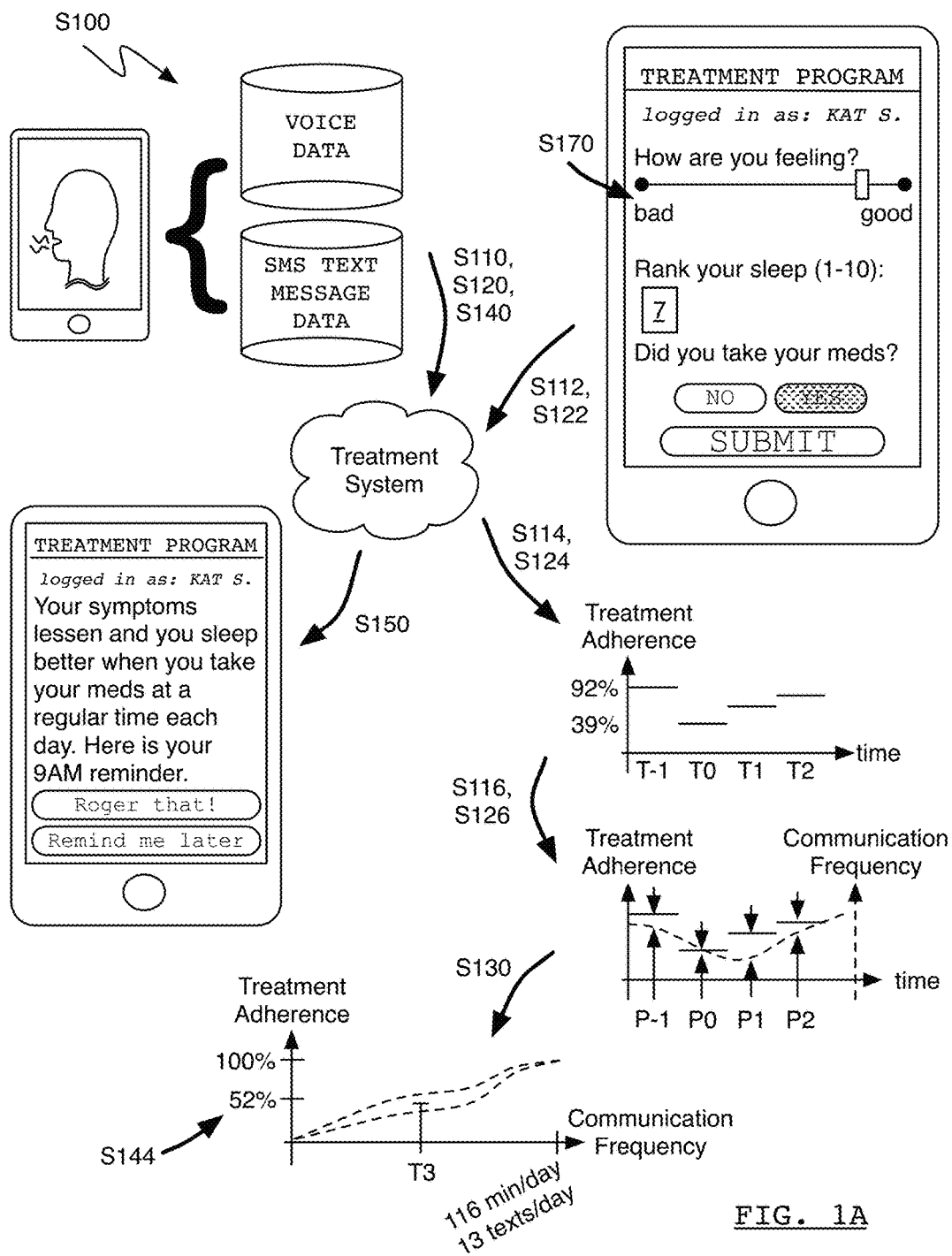
FIG. 1A is a flowchart representation of a first method of the invention.

As shown in FIG. 1A, a first method S100 for supporting a patient associated with a health condition through a treatment regimen includes: accessing a first log of use of a native communication application executing on a mobile computing device by the patient within a first time period in Block S110; receiving a first survey response corresponding to the first time period from the patient in Block S112; estimating a first adherence to the treatment regimen by the patient within the first time period based on the first survey response in Block S114; correlating the first log of use of the native communication application with the first adherence to the treatment regimen in Block S116; accessing a second log of use of the native communication application by the patient within a second time period in Block S120; receiving a second survey response from the patient within the second time period in Block S122; estimating a second adherence of the patient within the second time period based on the second survey response in Block S124; correlating the second log of use of the native communication application with the second adherence to the treatment regimen in Block S126; generating a patient regimen adherence model including the first log of use of the native communication application, the second log of use of the native communication application, the first adherence, and the second adherence in Block S130; accessing a third log of use of the native communication application by the patient within a third time period in Block S140; estimating a third adherence to the treatment regimen within the third time period based on the patient regimen adherence model and the third log of use of the native communication application in Block S144; and presenting a treatment-related notification based on the third adherence through the mobile computing device in Block S150.

Figure 1B:
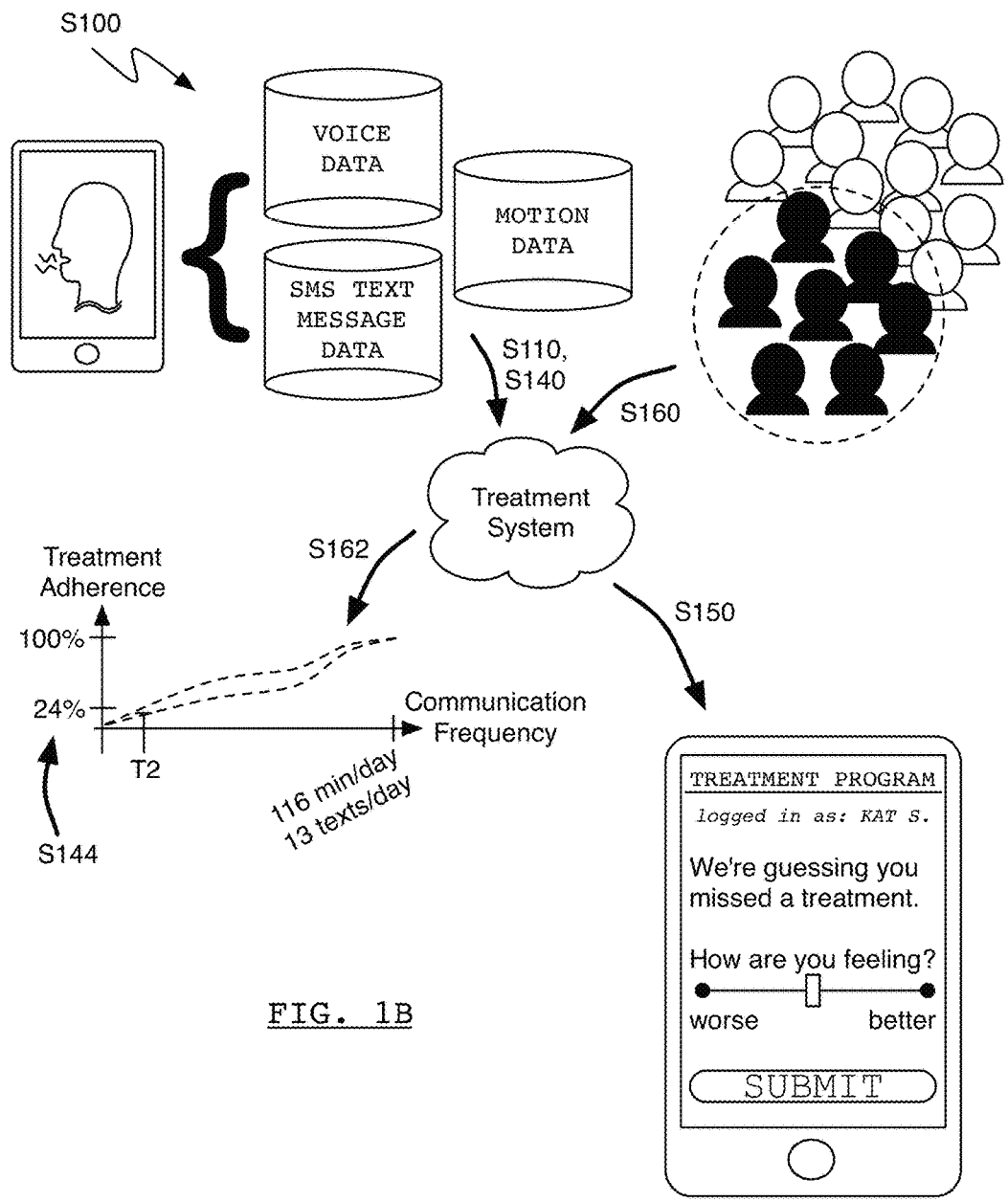
FIG. 1B is a flowchart representation of a variation of the first method.

As shown in FIG. 1B, one variation of the first method S100 includes: accessing a log of use of a native communication application executing on a mobile computing device by a patient in Block S110; selecting a subgroup of a patient population based on the log of use of the native communication application and a communication behavior common to the subgroup in Block S160; retrieving a regimen adherence model associated with the subgroup, the regimen adherence model defining a correlation between treatment regimen adherence and communication behavior for patients within the subgroup in Block S162; predicting patient adherence to the treatment regimen based on the log of use of the native communication application and the regimen adherence model in Block S144; and presenting a treatment-related notification based on the patient adherence through the mobile computing device in Block S150.

Figure 1C:
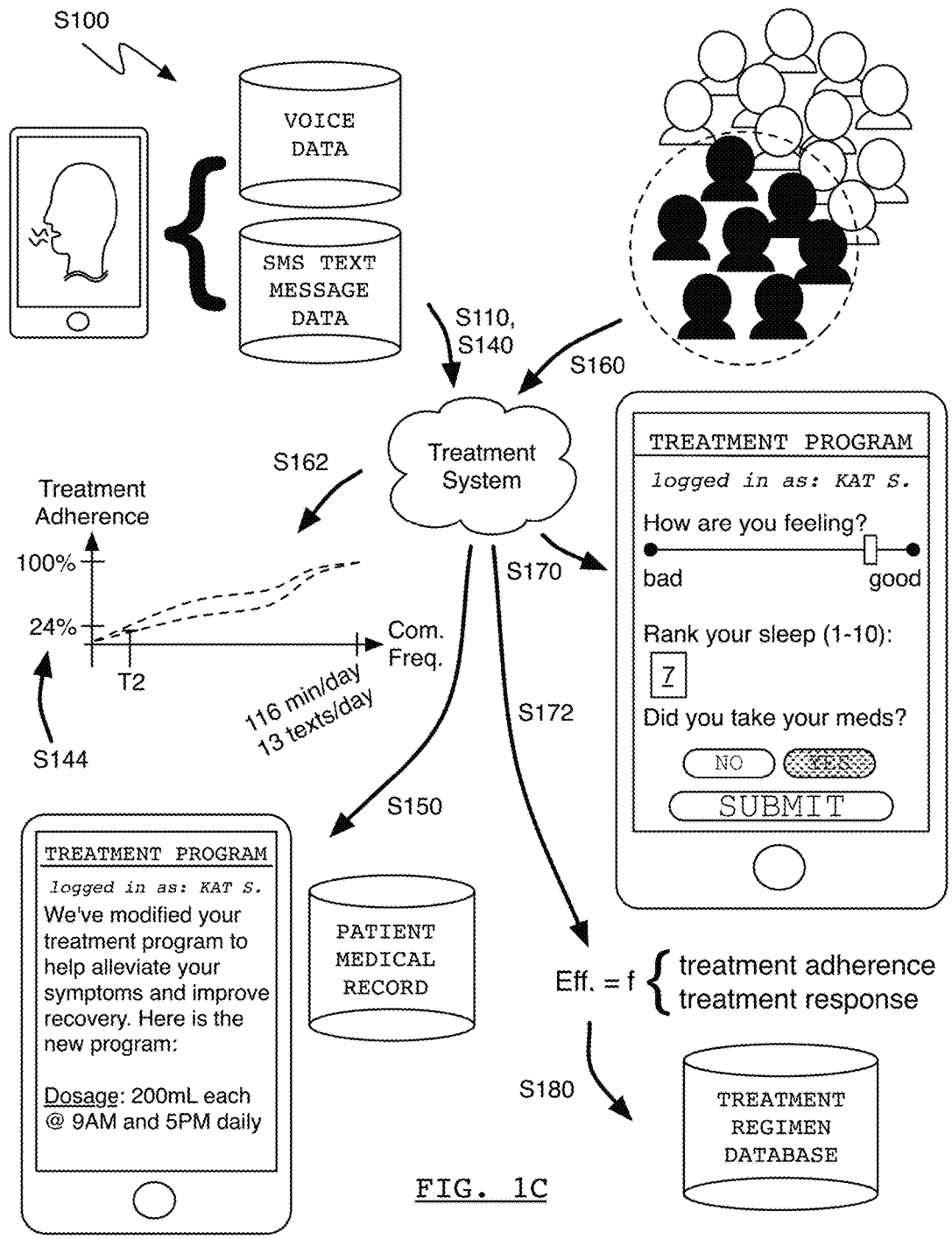
FIG. 1C is a flowchart representation of a variation of the first method.

As shown in FIG. 1C, another variation of the first method includes: accessing a log of use of a native communication application executing on a mobile computing device by a patient within a period of time in Block S110; selecting a subgroup of a patient population based on the log of use of the native communication application and a communication behavior common to the subgroup in Block S160; retrieving a regimen adherence model associated with the subgroup, the regimen adherence model defining a correlation between treatment regimen adherence and communication behavior for patients within the subgroup in Block S162; predicting adherence to the treatment regimen by the patient based on the log of use of the native communication application and the regimen adherence model in Block S144; extracting a treatment response of the patient from a patient survey corresponding to the period of time in Block S112; estimating an efficacy of the treatment regimen in treating a health condition of the patient according to a comparison between the treatment response and the adherence to the treatment regimen by the patient in Block S172; transmitting a notification to a care provider associated with the patient in response to the efficacy of the treatment regimen that falls below a threshold efficacy in Block S150.

Figure 1D:
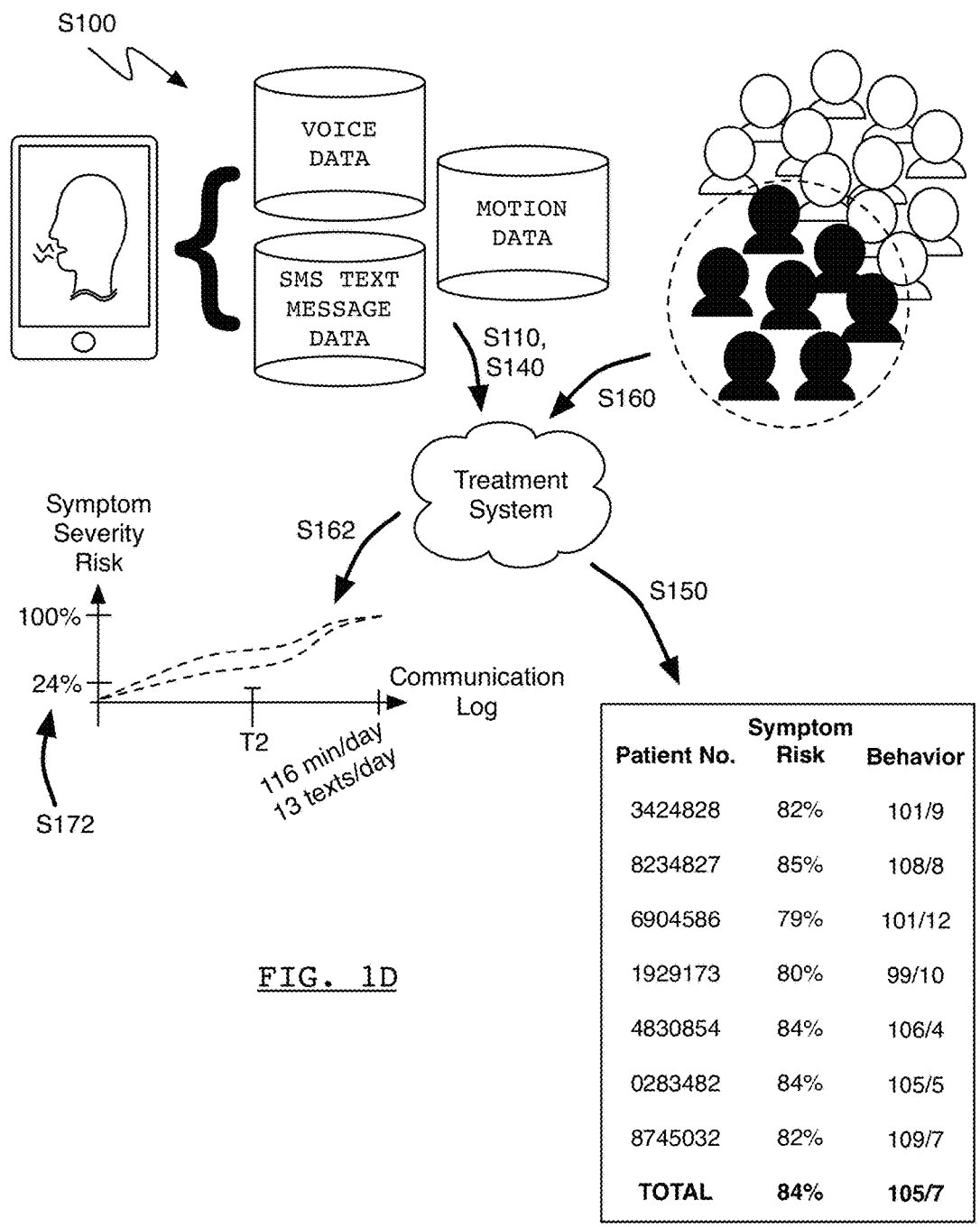
FIG. 1D is a flowchart representation of a variation of the first method.

As shown in FIG. 1D, yet another variation of the first method includes: accessing a log of use of a native communication application executing on a mobile computing device by the patient in Block S110; selecting a subgroup of a patient population based on the log of use of the native communication application and a communication behavior common to the subgroup in Block S160; retrieving a health risk model associated with the subgroup, the health risk model defining a correlation between risk of change in a medical symptom and communication behavior for patients within the subgroup in Block S162; predicting a risk of change in a medical symptom for the patient based on the log of use of the native communication application and the health risk model in Block S172; and transmitting a notification to a care provider associated with the patient in response to the risk of change in the medical symptom for the patient that exceeds a threshold risk in Block S150.

Figure 2A:
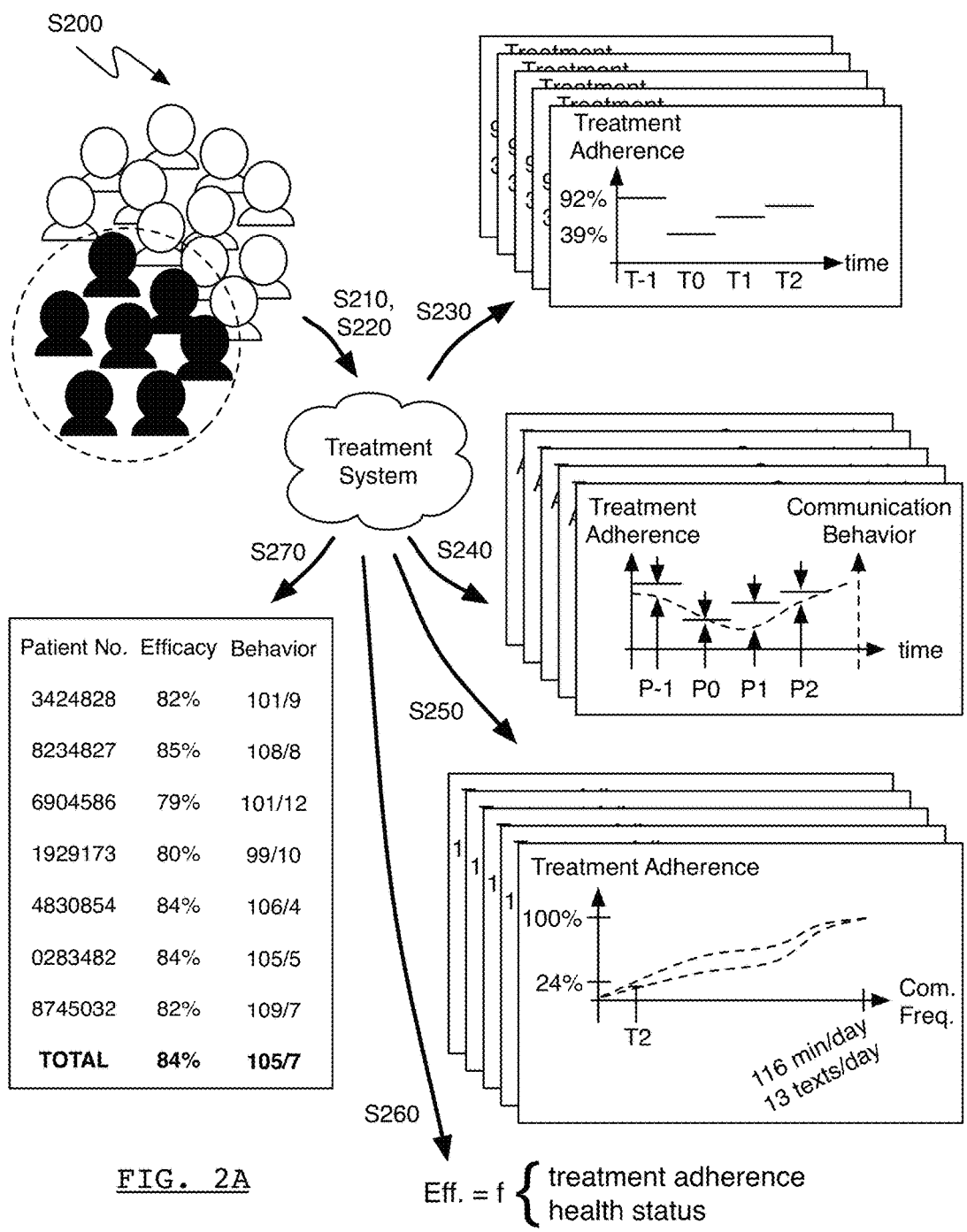
FIG. 2A is a flowchart representation of a second method of the invention.

As shown in FIG. 2A, a second method S200 includes: selecting a subgroup of patients from a patient population in Block S220, patients within the subgroup exhibiting similar behavioral characteristics and associated with a health condition; for a patient within the subgroup, estimating adherence of the patient to a prescribed treatment regimen during a period of time based on survey responses entered by the patient through a corresponding mobile computing device in Block S230; for a patient within the subgroup, characterizing communication behavior of the patient based on use of a native communication application executing on a corresponding mobile computing device by the patient during the period of time in Block S240; for a patient within the subgroup, correlating communication behavior of the patient with a health status of the patient in Block S250; estimating an efficacy of the treatment regimen in treating the health condition for patients within the subgroup based on adherence to prescribed treatment regimens and health statuses of patients within the subgroup in Block S260; and generating a treatment regimen report specific to the subgroup based on the efficacy of the treatment regimen in Block S270.

Figure 2B:
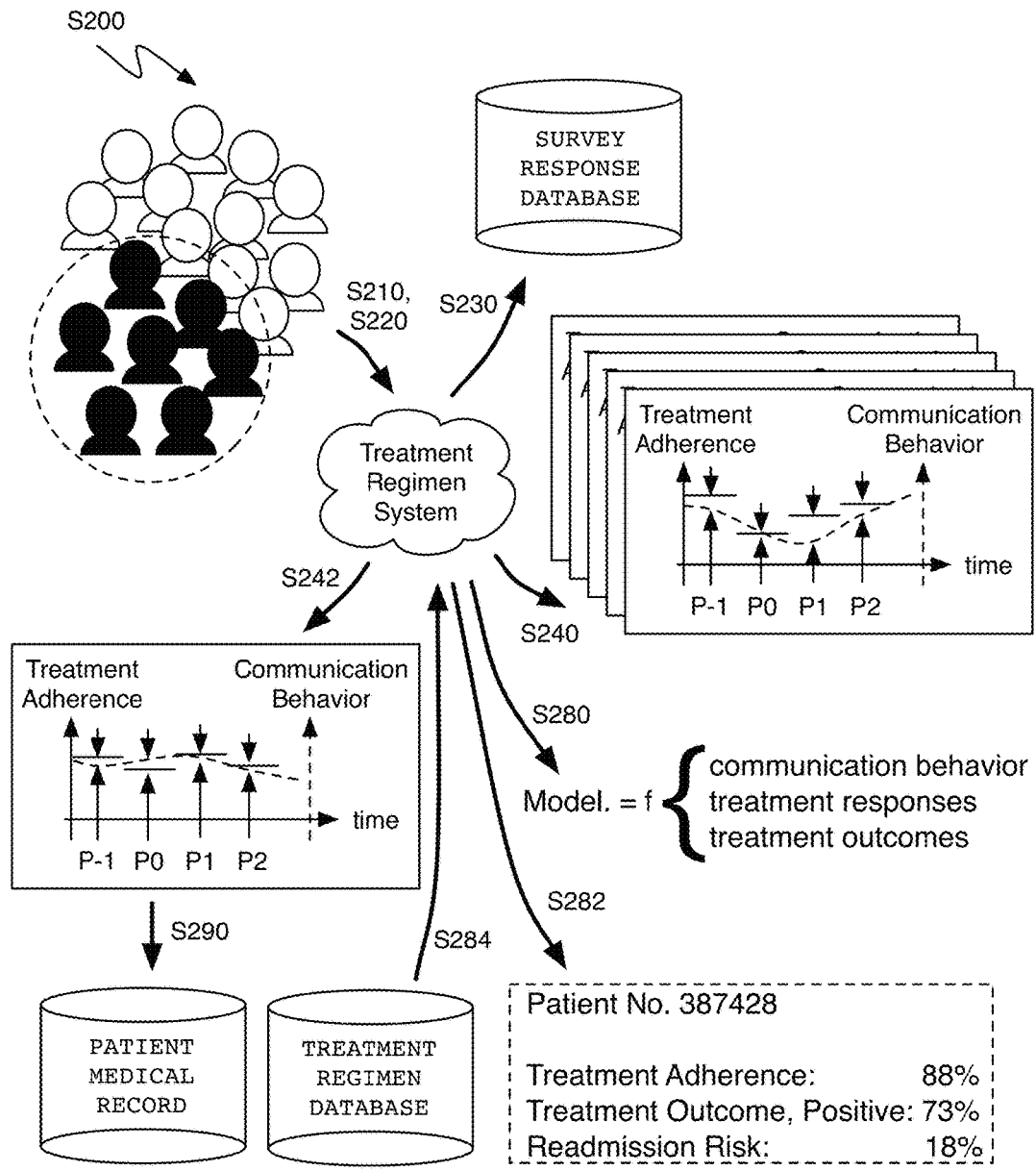
FIG. 2B is a flowchart representation of a variation of the second method.

As shown in FIG. 2B, one variation of the method includes: selecting a population of patients prescribed a treatment regimen for a health condition in Block S210; for a patient within the population, characterizing communication behavior of the patient based on use of a native communication application executing on a corresponding mobile computing device by the patient prior to initiation of a treatment regimen and during administration of the treatment regimen to the patient in Block S240; selecting a subgroup of patients from the population of patients based on similar communication behaviors prior to initiation of the treatment regimen in Block S220; extracting treatment responses from surveys completed by patients within the subgroup during administration of the treatment regimen in Block S230; generating a treatment regimen model for the subgroup in Block S280, the treatment regimen model defining a correlation between communication behavior, treatment responses, and treatment regimen outcomes for patients within the subgroup; characterizing communication behavior of a subsequent patient based on use of a native communication application executing on a corresponding mobile computing device by the subsequent patient in Block S242; and generating a predicted treatment regimen outcome for the subsequent patient based on a similarity between communication behavior of the subsequent patient and communication behavior common within the subgroup in Block S282.

Figure 2C:
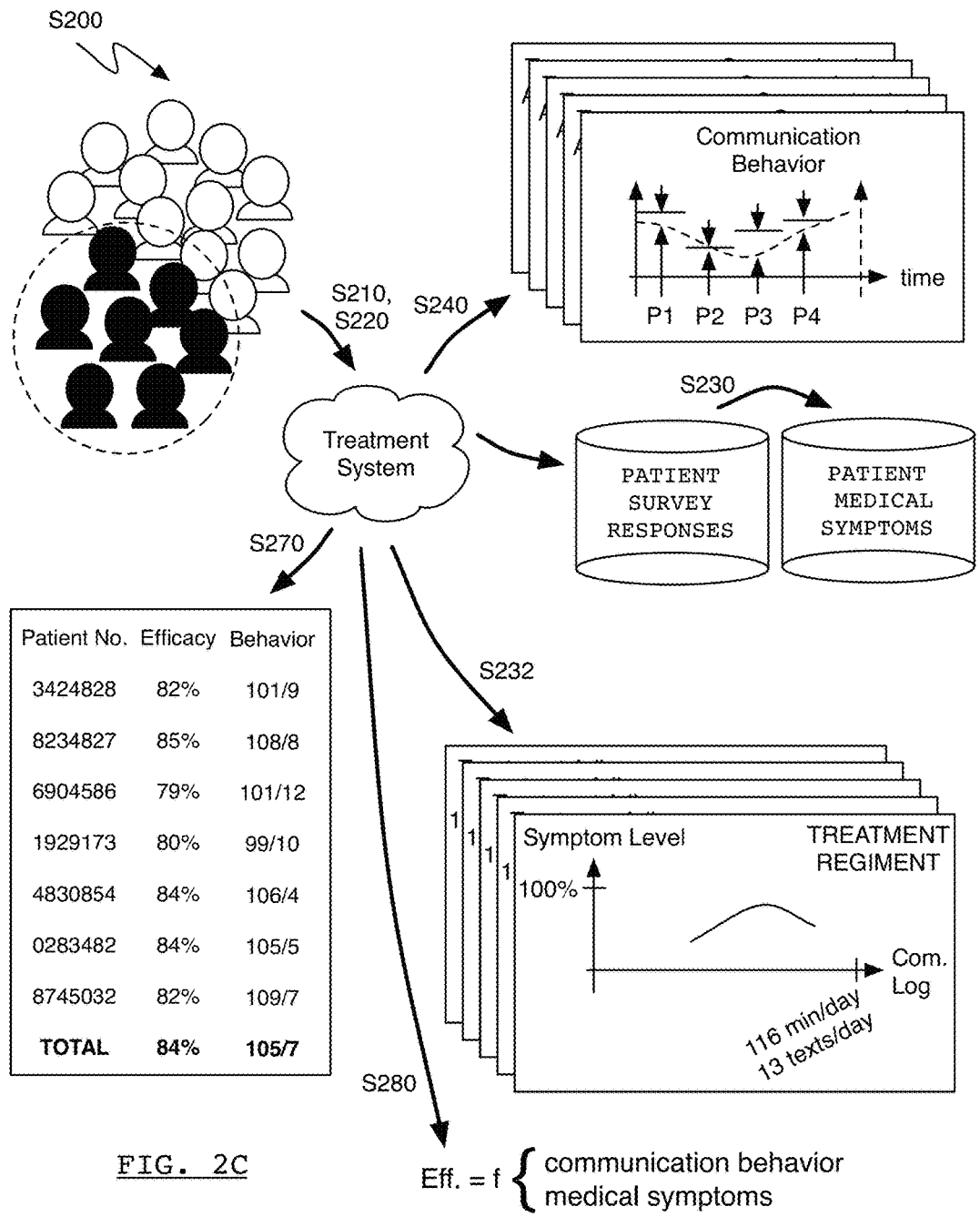
FIG. 2C is a flowchart representation of a variation of the second method.

As shown in FIG. 2C, another variation of the second method includes: selecting a subgroup of patients associated with a health condition from a population of patients, patients in the subgroup exhibiting similar behavioral characteristics in Block S220; for patients within the subgroup, characterizing communication behavior of a patient based on use of a native communication application executing on a corresponding mobile computing device by the patient during the period of time in Block S240; extracting characteristics of medical symptoms of patients within the subgroup from surveys submitted by patients within the subgroup in Block S230; identifying a relationship between communication behaviors of patients within the subgroup, characteristics of medical symptoms of patients within the subgroup, and a treatment regimen administered to patients within the subgroup in Block S232; generating a treatment efficacy model for the subgroup based on the relationship, the treatment efficacy model defining a correlation between a change in communication behavior and efficacy of the treatment regimen in alleviating medical symptoms of patients within the subgroup in Block S280.

Figure 2D:
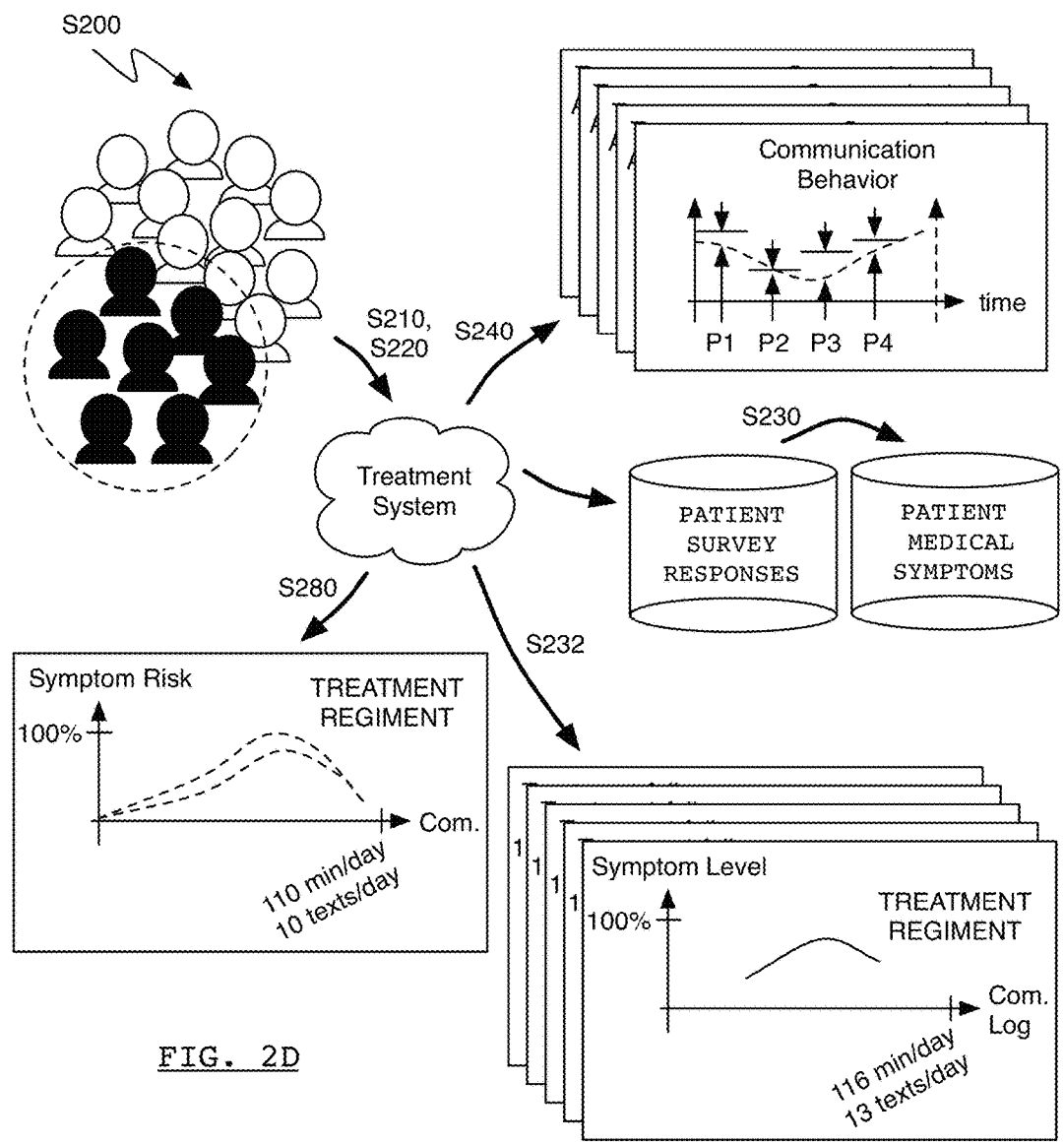
FIG. 2D is a flowchart representation of a variation of the second method.

As shown in FIG. 2D, yet another variation of the second method includes: selecting a subgroup of patients associated with a health condition from a population of patients, patients in the subgroup exhibiting similar behavioral characteristics in Block S220; for patients within the subgroup, characterizing communication behavior of a patient based on use of a native communication application executing on a corresponding mobile computing device by the patient during the period of time in Block S240; extracting characteristics of medical symptoms of patients within the subgroup from surveys submitted by patients within the subgroup in Block S230; identifying a relationship between communication behaviors of patients within the subgroup and characteristics of medical symptoms of patients within the subgroup in Block S232; generating a health risk model for the subgroup based on the relationship, the health risk model defining a correlation between a change in communication behavior and risk of change in a medical symptom in Block S280.

2. Applications of the Methods

Generally, the first and second methods S100, S200 function to collect communication data of a patient (a user or an at-risk individual) from a mobile computing device associated with the patient and to anticipate a health status of the patient based on the patient's communication data. The methods can subsequently apply the anticipated health status of the patient to suggest an action to the patient and/or to inform a nurse, care provider, a family member, a pharmacist, a pharmacologist, an insurance producer, a hospital, or other health professional or network, etc. with anticipated health-related information of the patient. The methods can additionally or alternatively implement an anticipated patient health status to drive automated or manual targeted intervention of for a patient via a phone call, email, health tip notification, insight, or other electronic communication. The methods can also apply an anticipated health status of a patient to remind the patient to fulfill a treatment, to model the patient's progress through a treatment program or regimen, to predict an outcome of the patient's treatment program, to modify or customize a treatment program for the patient, to generate a model of treatment regimens and/or treatment regimen outcomes for a group of similar patients within a population of patients, to predict or monitor a change in patient symptoms or health status change, etc., such as based on volunteered survey data and/or volunteered or predicted treatment regimen adherence by the patient and/or other similar patients.

In one example, over time, the methods collect data related to the patient's daily phone calls, text messages, and emails, including frequency, duration, length of time to respond to inbound communications, time-related communication patterns, and/or diversity of contacts through one or more native applications executing on a smartphone (or tablet) associated with the patient (e.g., a phone call application, a text messaging application, and an email application). Initially, the methods can survey the patient for his health risk assessment, symptom score, and/or degree of current symptoms (e.g., how the patient is feeling) and then correlate the patient's health status, symptom score etc. to generate a health risk model. For example, the methods can generate a quantitative risk score corresponding to a predicted level of risk of change in a medical symptom for a patient based on a correlation between patient behavior and a corresponding health risk model.

The methods can subsequently implement the health risk model to predict a level of the patient's symptoms at a later time and/or if a notification pertaining to the patient's health should be generated based (solely or predominantly) on the patient's communication behavior through a computing device. As in this example, the first method S100 can extrapolate a patient health status from patient communication data and survey responses and combine patient health status with patient communication behavior to generate a health risk model, and the first method can later anticipate a change in patient health risk by feeding subsequent patient communication data into the health risk model to determine subsequent patient health risk and generate a notification for the patient accordingly.

In another example, over time, the methods collect data related to the patient's daily phone calls, text messages, emails, and/or other inbound and/or outbound communications from the patient's mobile computing device, including frequency, duration, length of time to respond to an inbound communication, time-related communication patterns, diversity of contacts, etc. through one or more native communication applications executing on a smartphone (or tablet) associated with the patient (e.g., a phone call application, a text messaging application, and an email application). The methods can thus aggregate and manipulate any of the foregoing data to estimate patient adherence to a treatment regimen (e.g., whether the patient took his medications) and how the patient is 'feeling' (i.e., degree of symptoms) and subsequently correlate the patient's treatment adherence and feelings to the patient's communication behavior to generate a regimen adherence model. The methods can subsequently predict how the patient is feeling and/or if the patient followed his treatment regimen based on the patient's communication behavior through his smartphone. As in this example, the first method S100 can extrapolate patient treatment regimen adherence from a survey response, combine patient treatment regimen adherence with patient communication behavior to generate a regimen adherence model, and later anticipate a patient regimen adherence by feeding subsequent communication behavior into the regimen adherence model and then generate a notification for the patient accordingly.

In a similar example, the methods apply behavior data of the patient, such as prior to and/or during a treatment program or regimen, to select a regimen adherence model associated with a subgroup of patients exhibiting communication behaviors similar to those of a particular patient. By feeding patient communication behavior data into a health risk model, the methods can thus predict how the patient is feeling (i.e., presentation of the patient's symptoms) without additional patient info (e.g., additional survey results). As in this example, the methods can thus combine survey responses and patient communication behaviors to generate patient population subgroup models and later anticipate a patient health risk—and generate a notification accordingly—by feeding subsequent communication behavior of a patient into the model(s).

In yet another example, the first method S100 applies behavior data of the patient, such as prior to and/or during a treatment program or regimen, to select a regimen adherence model associated with the subgroup exhibiting communication behaviors similar to those of the patient. By feeding subsequent patient communication behavior into the regimen adherence model, the first method S100 can thus predict how the patient is feeling (i.e., presentation of the patient's symptoms) at a particular time and/or anticipate how or when the patient is fulfilling his treatment regimen, such as by consuming the prescribed medications at prescribed times and at prescribed dosages, without additional patient info (e.g., additional survey results). As in this example, this variation of the first method S100 can thus extrapolate patient treatment regimen adherence from a survey response, combine patient treatment regimen adherence with patient communication behavior to select a patient population subgroup and a related regimen adherence model, and later anticipate a patient regimen adherence by feeding subsequent communication behavior into the regimen adherence model and then generate a notification for the patient accordingly.

In still another example, the methods implement behavior data of a patient to select a health risk model associated with a particular subgroup exhibiting communication behaviors similar to those of the patient. By feeding subsequent patient communication behavior data into the health risk model, the methods can this predict how the patient is feeling (i.e., presentation of the patient's symptoms) at a particular time and/or anticipate how or when the a notifications indicating patient risk should be transmitted to a care provider, all without necessitating additional patient information (e.g. additional survey results).

In a further example, the first method S100 applies behavior data of the patient, such as prior to and/or during a treatment program or regimen, to select a regimen adherence model associated with the subgroup exhibiting communication behaviors similar to those of the patient. By feeding subsequent patient communication behavior into the regimen adherence model, the first method S100 can thus predict how the patient is feeling (i.e., presentation of the patient's symptoms) at a particular time and/or anticipate how or when the patient is fulfilling his treatment regimen, such as by consuming the prescribed medications at prescribed times and at prescribed dosages, without additional patient info (e.g., additional survey results).

In another example, the second method S200 collects communication data from multiple patients, groups patients according to identified communication behaviors, and anticipates progress through a treatment program and the effects of the treatment program on patients with a selected group. Rather than relying on data entered manually by patients and/or care providers, estimating patient activity or action from motion data (which can be imprecise, require substantial computing powers, and lack suitable precision for the health care space), etc., the second method S200 can instead generate models linking treatments (e.g., pharmacotherapy regimens, physical therapy programs) to symptom presentation and final health condition outcome for patients based on how, when, and/or with whom, etc. patients communicate over time (e.g., on a daily or four-hour basis). In this example, the second method S200 can thus select a subgroup of patients within a patient population based on communication behaviors of the patient population, estimate treatment regimen adherence within the subgroup based on survey responses volunteered by patients within the subgroup, estimate the health status of patients within the subgroup based on communication behaviors of the patients, and combine treatment adherence and communication behavior of patients within the subgroup to estimate the efficacy of the treatment regimen specifically for the subgroup of patients.

In the foregoing example, the second method S200 can further apply such models to particular patients to anticipate how a patient will respond to a treatment regimen and/or to customize a treatment regimen for the patient based on similarities and/or differences between the patient's communication behaviors and communication behavior of other patients (e.g., previous or current patients with similar diagnosed health conditions and/or prescribed treatment regimens).

The first and second methods S100, S200 can therefore derive meaningful health-related data for individual patients and/or groups of patients from patient communication behaviors extrapolated from phone call, text message, email, and/or other communication data collected passively through mobile computing devices associated with the patient(s). Such derived health-related data can be implemented within a patient's mobile computing device to privately guide a patient through a treatment program by a care provider to anticipate risk of increasing medical symptoms or risk of a change in health status of the patient, by a doctor to monitor a patient's progress or to modify a prescription, by a nurse to identify a need to provide manual support to the patient, and/or by a pharmacologist to research drug therapies and drug responses within a population, etc. For example, Blocks of the first and second methods S100, S200 can be implemented to collect patient data for an experiment, a research study, a commercial launch, a marketing study, a patient community study, such as on the recommendation of a healthcare provider (e.g., a doctor or a medical institution (e.g., a hospital center) to improve patient care. In this example, the first and second methods S100, S200 can interface with a patient-facing interface, a doctor-facing interface, a nurse-facing interface, and/or a pharmacologist-facing interface, etc. to deliver notifications and related data to the patient, doctor, nurse, pharmacologist, and/or other care provider directly or indirectly associated with the patient. In another example, the first and second method S100, S200 can be implemented on a computing device associated with a particular patient as a personal heath-tracking tool.

In one implementation, the first and second methods S100, S200 interface with a native data collection application executing on a patient's mobile computing device (e.g., smartphone, tablet, personal data assistant (PDA), personal music player, vehicle, etc.) to retrieve patient communication data. For example, the native data collection application can be installed on the patient's mobile computing device, execute substantially continuously while the mobile computing device is in use and/or "ON," record times, durations, and contact types (e.g., family, friend, coworker, business associate) of each inbound and outbound communication from the patient's mobile computing device. The mobile computing device can then upload this data to a remote database, such as in real-time, every hour, at the end of each day, etc. over an Internet connection, and the first and/or second method, implemented on a computer network (e.g., the "cloud"), can retrieve the patient's communication data from the remote database, analyze the patient's communication data to anticipate the patient's symptoms and/or therapy adherence, and generate a notification for the patient, and the patient's mobile computing device can download and subsequently display the notification for the patient, actions that can be handled automatically and in the background by the native data collection application or an alternative patient-facing native application executing on the mobile computing device. The computer network can additionally or alternatively generate a patient regimen adherence model, a patient outcome model, a patient behavioral model, a health risk model etc. and transmit any one or more models to a doctor, a nurse, a pharmacologist, a therapist, etc.

Therefore, Blocks of the first and second methods S100, S200 can be implemented on one or more computer systems, such as a cloud-based computer system (e.g., Amazon $EC_3$), a mainframe computer system, a grid-computer system, or any other suitable computer system. Blocks of the first and second methods S100, S200 can collect patient data from one or more devices over the Internet, such as communication data directly from a natively application executing on the patient's smartphone and/or motion data from a wearable sensor collected by the patient's smartphone and then uploaded to a remote database over an Internet connection. Collection, manipulation, and transmission of patient data in Blocks of the first and second methods S100, S200 can further adhere to health-related privacy laws, such as by privatizing or anonymizing patient data and transmitting encrypted or private notifications—such as pertaining to a patient's therapy adherence—to the patient and/or a doctor, a nurse, a pharmacologist, a researcher, etc. associated with the patient.

As in the foregoing implementation, when a patient installs and/or authorizes collection and transmission of personal communication data through such a native data collection application, the native application can prompt the patient to create a profile or account. The account can be stored locally on the patient's mobile computing device and/or remotely on the computer network and can contain a name, age, gender, location, occupation, list of health conditions, list of current health-related treatments and medications, medical history, a primary care physician (including name, office, contact information, etc.), health insurance information, prescription insurance plan, local pharmacy information, or other demographic and/or health-related information, any of which can be added by the patient, a family member, a doctor, a nurse, or other individual associated with the patient and/or retrieved from a medical, insurance, social network, or other related database. The first and second methods S100, S200 can also update the patient's account with additional patient information over time, such as presentation of symptoms, estimated patient treatment adherence, and/or predicted treatment regimen outcome for the patient.

Blocks of the methods can function to qualify and/or quantify a correlation between a health outcome or symptom risk and observed behavior changes for a patient based on data gathered passively from a patient's mobile computing device (e.g., mobile phone, smartphone and/or tablet, etc.) substantially without manual data entry from the patient, a doctor, a nurse, a pharmacist, etc. Blocks of the methods can similarly quantify a correlation between a patient health status and an observed patient behavior gathered from the patient's mobile computing device and further combine passive behavior data collection with self-reported patient data (i.e., survey responses) to enhance the quality of a health-related model, extrapolated health-related notification triggers, patient inferences, patient symptom risk predictions, etc. for an individual patient and/or for a subgroup of patients. In particular, the first and second methods S100, S200 can identify a relationship between a health outcome and a communication-related behavior change (e.g., a change in the frequency of phone calls, text messages, and emails over a preset period of time), such as changes in a patient's communication behavior from prior to administration of a treatment to during and/or after administration of the treatment for the patient.

The first and second methods S100, S200 can also identify a correlation between health outcome and patient activity data (i.e., accelerometer and gyroscope data from a corresponding mobile device or wearable sensor), local environmental data, patient location data, patient survey data, etc. The first and second methods S100, S200 can then implement an identified relationship between a (communication) behavior change and a change in a patient's health or quality of life over a period of time to anticipate a change in patient health risk, trigger or target an automated or manual intervention (e.g., an automated notification) to assist the patient through a treatment regimen, anticipate symptom relapse and estimate risk of hospital readmission for the patient, etc. The methods can similarly implement the foregoing identified relationship to identify categories, clusters, or subgroups of similar patients within a patient population, to modify or customize treatment regimens or patient health risk models for particular patient clusters, to prescribe a customized or subgroup-specific treatment regimen to a subsequent patient, to assist a care provider in patient triage, to support or justify adjustment to health care utilization, to compare health outcomes (e.g., admission/readmission rates and health care utilization) within and/or across a patient population, etc. . . . . The methods can thus function to improve health outcomes for a particular patient and/or within a subgroup of a patient population and to improve health care utilization.

Generally, the first and second methods S100, S200 can function to qualify and/or quantify a correlation between a health outcome related to a treatment, therapy, and/or medication, etc. and observed behavior changes based on data gathered passively from a patient's mobile computing device (e.g., mobile phone, smartphone and/or tablet, etc.) substantially without manual data entry from the patient, a doctor, a nurse, a pharmacist, etc. The first and second methods S100, S200 can similarly quantify a correlation between a patient health status and an observed patient behavior based on patient data gathered from the patient's mobile computing device and combine passive behavior data collection with self-reported patient data (i.e., from surveys) to enhance the quality of a treatment regimen, inferences, and treatment predictions for a patient and/or a subgroup of patients. In particular, the first and second methods S100, S200 can identify a relationship between a health outcome and a communication-related behavior change (e.g., phone calls, text messages, emails), such as changes in a patient's communication behavior from prior to administration of a treatment to during and/or after the treatment for an individual patient. The methods can also identify a change in composite work-life balance for the patient, such as based on time spent by the patient in work-related phone calls or sending work-related emails or at a physical office or work location relative to a total communication time of the patient, a total patient waking time per day, or an amount of time spent at home. The methods can thus correlate a change in patient composite work-life balance with a declining patient health status or increased patient health risk (e.g., for recurring or symptoms of increased severity) based on the health risk model. Similarly, the methods can compute a composite quality of life score for the patient, based on time spent in phone calls and at physical locations related to social events, familial and work phone calls, and work locations and transitions between such locations, and the methods can correlate a change in composite quality-of-life with a declining patient health status or increased patient health risk based on the health risk model.

The first and second methods S100, S200 can additionally determine a correlation between health outcome and patient mobile phone usage (i.e. screen unlocks, mobile application use) derived from an operating system or the task manager executing on the patient's mobile computing device to determine periods of patient activity, hyper-activity (e.g. frequent unlocks late at night when the patient is unable to sleep), and inactivity. The first and second methods S100, S200 can then implement an identified relationship between a mobile usage behavior change and a change in a patient's health or quality of life over a period of time based on a corresponding health risk model.

The first and second methods S100, S200 can also determine a correlation between health outcome and patient activity data (i.e., accelerometer and gyroscope data from the mobile computing device or external wearable sensor), local environmental data, patient location data, patient survey data, etc. The first and second methods S100, S200 can then implement an identified relationship between a (communication) behavior change and a change in a patient's health or quality of life over a period of time to anticipate a treatment efficacy and/or patient response to a treatment, estimate a patient's treatment adherence (i.e., compliance), determine patient satisfaction in a treatment, trigger or target automated or manual interventions (e.g., automated notifications) to assist a patient through a treatment, anticipate symptom relapse and estimate risk of hospital readmission. The first and second methods S100, S200 can similarly implement such an identified relationship to identify categories, clusters, or subgroups of similar patients within a patient population, to modify or customize treatment regimens or notifications for particular patient clusters, to prescribe a customized or subgroup-specific treatment regimen to a subsequent patient, to assist a care provider in patient triage, to support adjustment health care utilization, to compare treatment outcomes (e.g., admission/readmission rates and health care utilization) within and/or across a patient population, etc. to improve treatment outcomes, therapy efficacy, and adherence to a treatment program for a particular patient and/or within a subgroup of a patient population, and health care utilization.

Though the following description describes the inventions particularly in the context of monitoring and/or estimating treatment adherence, Blocks of first and second methods S100, S200 can implement similar functionality and techniques to identify patient risk and assess treatment efficacy.

3. Behavior Data

Block S110 of the first method S100 recites identifying a first log of use of a native communication application executing on a mobile computing device by the patient within a first time period. Block S120 and Block S140 similarly recite identifying a second log and a third log of use of the native communication application by the patient within a second and a third time period, respectively. Generally, Blocks S110, S120, and S140 function to unobtrusively collect and/or retrieve communication-related data from a patient's mobile computing device, such as through integration within or by interfacing with a native data collection application to collect patient data, as described above. For example, the native data collection application can launch on the patient's mobile computing device as a background process that gathers patient data once the patient logs in to his account. In particular, Block S110, etc. collects communication data and/or native communication application usage data, generated by the patient's mobile computing device, to identify how and how often (i.e., with what frequency) the patient interacts with and communicates with other individuals through phone calls, e-mail, instant messaging, an online social network, etc.

In one implementation, Block S110, etc. collects phone call-related data, including a number of sent and/or received calls, call duration, call start and/or end time, location of patient before, during, and/or after a call, and number and times of missed or ignored calls. Block S110, etc. can also collect text messaging (e.g., SMS test messaging) data, including number of messages sent and/or received, message length, message entry speed, efficiency, and/or accuracy, time of sent and/or received messages, and location of the patient when receiving and/or sending a message. Block S110, etc. can collect similar types of data on textual messages sent through other communication venues, such as public and/or private textual messages sent to contacts of the patient through an online social networking system, reviews of products, services, or businesses through an online ranking and/or review service, and/or any other text-based communication generated by the patient and communicated to another individual and/or computer network.

Block S110, etc. can further collect location data of the patient before, during, and/or after (or in the absence of) communication with another individual (e.g., a phone call) and/or computer network (e.g., a social networking message), such as by retrieving a GPS location from a GPS sensor within the patient's mobile computing device, estimating the location of the patient's mobile computing device through triangulation of local cellular towers, or identifying a geo-located local Wi-Fi hotspot, etc., during a phone call. Block S110, etc. can apply this data to track patient behavior characteristics, such as patient mobility, periods of patient isolated, patient work-life (e.g., balance based on time spent at specific locations), etc. Block S110, etc. can also collect patient location data before, during, and/or after communication with another individual, such as via a phone call and/or over a computer network (e.g., with a social networking message), and merge patient location with patient communication (or other) data. Block S110, etc. can therefore track the patient's mobility during a communication. Block S110, etc. can additionally or alternatively collect data pertaining to individuals in contact with the patient during the first period of time, etc., such as an individual's location during a phone call, phone number, contact duration and/or type with the patient, relationship to the patient or patient contact group (e.g., top contact, spouse, family member, friend, coworker, business associate, etc.) specified by the patient or learned from previous patient communications, etc.

Blocks S110, S120, etc., can further capture mobile usage data like screen unlocks and mobile application usage, such as by retrieving usage information from mobile operating system logs or task manager on the mobile computing device. Blocks of the methods can therefore track variations and periods of activity and inactivity for a patient through data automatically collected on the patient's mobile computing device, such as to estimate extended periods when the patient was hyperactive on the device or not asleep.

In one implementation, Block S110, etc. also collects or retrieves patient physical activity- or physical action-related data (e.g., accelerometer and gyroscope data), local environmental data, patient nutrition or diet-related data, etc. such as recorded through sensors within the patient's mobile computing device or through a wearable or other peripheral device in communication with the patient's mobile computing device. For example, a wireless-enabled scale, blood pressure sensor, and a pulse-dosimeter sensor can transmit the patient's weight, blood pressure, and blood oxygen level to the patient's mobile computing device, and Block S110 can add this data to the patient's account to further augment patient behavior data.

Block S110 can subsequently aggregate phone, text message, email, social networking, and/or other patient communication data for a particular period of time into a qualitative and/or quantitative feature for the patient for the particular time period. The feature can be specific to a day, a week, a month, a day period (e.g., morning, afternoon, evening, night), a time block during a day (e.g., one hour), a specific communication action (e.g., a single phone call, a set of communication actions of the same type (e.g., a set of phone calls within a two-hour period), all communications within a period of time, etc.). For example, Block S110 can generate a weighted composite of the frequency, duration (i.e., length), timing (i.e., start and/or termination), and contact diversity of all outgoing voice (e.g., phone call) communications and a frequency, length, and timing and/or response time to (i.e., time to accept) incoming voice communications within the first period of time through a phone call application executing on the patient's mobile computing device. Block S110 can additionally or alternatively assess incoming and/or outgoing textual communications from a textual messaging application executing on the mobile computing device. Block S110 can also generate a quantitative assessment of a frequency of, a duration of, and a response time to both incoming and/or outgoing phone calls and textual communications to the mobile computing device during the first time period as a single qualitative and/or quantitative feature corresponding to the first period of time. Block S120 and/or S140 can implement similar methods to generate a feature for the second period of time and third period of time, respectively.

Blocks S112, S122, etc. can further extract features based on voice communications, textual communications, mobile application activity usage, location data, etc., which can be based on variance, entropy, or other mathematical and probabilistic computations of basic data, such as a composite activity score, a composite socialization score, a work-life balance score, a quality-of-life score, etc.

In one example, Block S110 implements machine learning, data mining, and statistical approaches to process patient communication data into relevant patient communication behavior features (e.g., data points). Block S110 can implement similar techniques to similarly process patient motion data, local environmental, and other automatically/passively collected data.

Block S240 of the second method S200 recites, for patients within the subgroup, characterizing communication behavior of a patient based on use of a native communication application executing on a corresponding mobile computing device by the patient during the period of time. Block S240 can thus implement functionality similar to Block S110, Block S120, etc. to extrapolate patient communication behavior from phone calls, text messages, social networking communications, emails, and/or other communications originating and/or terminating through one or more communication applications executing on one or more mobile computing devices associated with one or more patients. In one example, Block 240 characterizes communication behavior of multiple patients based on use of native communication applications executing on corresponding mobile computing devices by the patients both prior to initiation of and during administration of an action item specified in an automated notification directed to the patient and/or an associated nurse, doctor, care provider, etc. In another example, Block S240 characterizes communication behavior of multiple patients based on use of native communication applications executing on corresponding mobile computing devices by the patients both prior to initiation of similar treatment regimens and during administration of the treatment regimens.

Block S242 of the second method, which recites characterizing communication behavior of a subsequent patient based on use of a native communication application executing on a corresponding mobile computing device by the subsequent patient, can also implement such functionality to characterize communication behavior of a new (i.e., subsequent) patient. For example, Block S242 can pass the communication behavior characterization of the new patient to Block S282, and Block S282 can determine a similarity between the new patient and a subgroup of patients based on communication behaviors of the two and, from this determined similarity and an effectiveness of the health-related notifications within the subgroup, generate a health-related notification for the new patient. In another example, Block S242 passes the communication behavior characterization of the new patient to Block S282, wherein Block 282 determines a similarly between the new patient and a subgroup of patients based on communication behaviors of the two and, from this determined similarity, predicts an effectiveness in a treatment regimen for the new patient based on the effectiveness of the treatment regimen within the subgroup.

However, Blocks S110, S120, S140, S240, S242, etc. can function in any other way to identify and/or characterize use of a native communication application by a patient within a period of time.

4. Surveys

Block S112 of the first method S100 recites receiving a first survey response corresponding to the first time period from the patient. Block S122 similarly recites receiving a second survey response from the patient within the second time period. Generally, Block S112, etc. functions to prompt the patient to self-report additional health-related data that can be implemented within the first and/or second method S200 to qualify patient communication data, such as to teach a patient regimen adherence model relating patient communication to patient treatment adherence and/or patient symptom presentation. For example, Block S112 transmits a survey to the patient's mobile computing device, the native data collection application executing on the mobile computing device opens the survey and prompts the patient to enter relevant data, and Block S112 receives patient responses to the survey from the mobile computing device once the survey is complete. In this example, Block S170 can function to extract a treatment response of the patient from a corresponding survey.

Block S112 can generate the survey that includes prompts to enter a pain level (e.g., on a body-location-specific basis), presentation of symptoms (e.g., on a health-condition-specific basis), adherence to a treatment regimen (e.g., if and when the patient took a prescribed medication of some dosage), changes in presentation of symptoms after a treatment, how the patient "feels" generally, experience with a treatment and corresponding effect, a mood, a sleep quality or wakefulness, etc. The survey can also prompt the patient to supply information related to a diagnosed disease or condition, such as major depressive disorder, diabetes, or chronic obstructive pulmonary disease. Alternatively, Block S112 can retrieve relevant patient health data from a medical record, history, or profile of the patient. In one example, Block S112 can import a patient medication record from an Electronic Medical Records (EMR) system hosted by a healthcare provider or health insurance company, such as via a supported Application Programmable Interface (API).

Surveys can be presented to the patient on the mobile computing device at preset or patient-selected launch times and/or frequency. For example, Block S112 can prompt the patient to fill out a two-question survey every morning at 9:00 or after each meal, including whether he has taken prescribed medication(s) and his overall satisfaction with the treatment in mitigating symptoms. Alternatively, presentation of surveys can be triggered by a determined patient behavior or symptom change. In one example, Block S112 can trigger presentation of a survey to the patient in response to a disparity in actual and anticipated patient communication behavior, such as significantly more or significantly less phone call time by the patient than expected based on past patient communication behavior. In another example, Block S112 can trigger delivery of a pain survey launched within the application either at a pre-determined time and/or once a period of time (e.g., 72 hours) transpires without a detected change in the patient's location (e.g., the patient has not left his house) and/or without a detected phone call initiated by the patient.

Surveys can include a single or combination of question-and-answer types, such as multiple choice questions each with a single answer option, multiple choice questions each with multiple answer options, textual or numerical manual entry, slider (e.g., for easy number or level selection from a range), icon animation selection (e.g., icons indicating different intensities or symptoms), etc., as shown in FIG. 1A. For example, a survey can include a Patient Health Questionnaire (PHQ9), a WHO Wellbeing Index (WH05), or a one-question Pain Rating Scale question.

Block S112 can additionally or alternatively generate a prompt targeted at a family member, care providers, health organization, etc. associated with the patient. For example, Block S112 can prompt and collect survey responses from a nurse, including manually-entered patient symptom and treatment data. Alternatively, Block S112 can retrieve this information from the personal mobile computing device of a family member of the patient. Block S112 can similarly prompt a pharmacist or pharmacologist associated with the patient's treatment to enter patient prescription data directly into a survey. Alternatively, Block S112 can retrieve this data automatically from an associated pharmacy database. Yet alternatively, Block S112 can collect patient treatment data from a third-party system or device used by the patient or associated care provider, such as an Internet-enabled pillbox with embedded sensors.

Block S112 can further function to compensate the participant for completing a survey, such as with cash, a gift card, a pharmacy discount, a health insurance discount, etc., such as in an application of the first and/or second method S200 in which patient data is supplied to pharmaceutical researches to generate treatment regimens.

Block S112 can be implemented within the native data collection application, on a computer network in communication with the mobile computing device (e.g., via an Internet connection), or in any other suitable way. Block S122, etc. can implement similar techniques or functions, though Block S112, Block S122, etc. can function in any other way to collect survey responses corresponding to various time periods from the patient.

5. Data Storage

The first and second methods S100, S200 can store data locally on the patent's mobile computing device and/or in a remote database on a computer network. For example, private health-related patient data can be stored temporarily on the patient's mobile computing device in a locked and encrypted file folder on integrated or removable memory. In this example, the patient's data can be encrypted and uploaded to the remote database once a secure Internet connection is established. However, patient data can be stored on any other local device or remote data in any other suitable way and transmitted between the two over any other connection via any other suitable communication and/or encryption protocol.

6. Treatment Adherence

Block S114 of the first method S100 recites estimating a first adherence to the treatment regimen by the patient within the first time period based on the first survey response. Block S124 of the first method S100 similarly recites estimating a second adherence of the patient within the second time period based on the second survey response. Furthermore, Block S230 of the second method S200 recites, for patients within the subgroup, estimating adherence of a patient to a prescribed treatment regimen during a period of time based on survey responses entered by the patient through a corresponding mobile computing device. Generally, Blocks S114, S124, S230, etc. function to extract the patient adherence to a treatment regimen over time from corresponding survey responses collected in Blocks S112, S122, etc. For example, a survey can include an explicit inquiry into if, when, and in what dosage the patient took a medication specified in a pharmacotherapy regimen and/or if the patient completed and the duration of a physical therapy session, and Block S114 can identify the patient's response to the prompt, compare the patient's response to a treatment regimen assigned to the patient for the corresponding time period, and thus determine if and/or to what extent the patient fulfilled the treatment regimen for the corresponding time period. Block S114 can subsequently pass the degree of patient adherence to the treatment regimen to Block S116. Block S124 and Block S230, etc. can implement similar functionality.

Block S116 of the first method S100 recites correlating the first log of use of the native communication application with the first adherence to the treatment regimen, and Block S126 similarly recites correlating the first log of use of the native communication application with the first adherence to the treatment regimen, and Block S126 recites correlating the second log of use of the native communication application with the second adherence to the treatment regimen. Generally, Block S116, Block S126, etc. function to define a relationship between a degree of patient adherence to a treatment regimen and a quality and/or quantity of communication (i.e., communication behavior) of the patient for a corresponding period of time.

Figure 4:
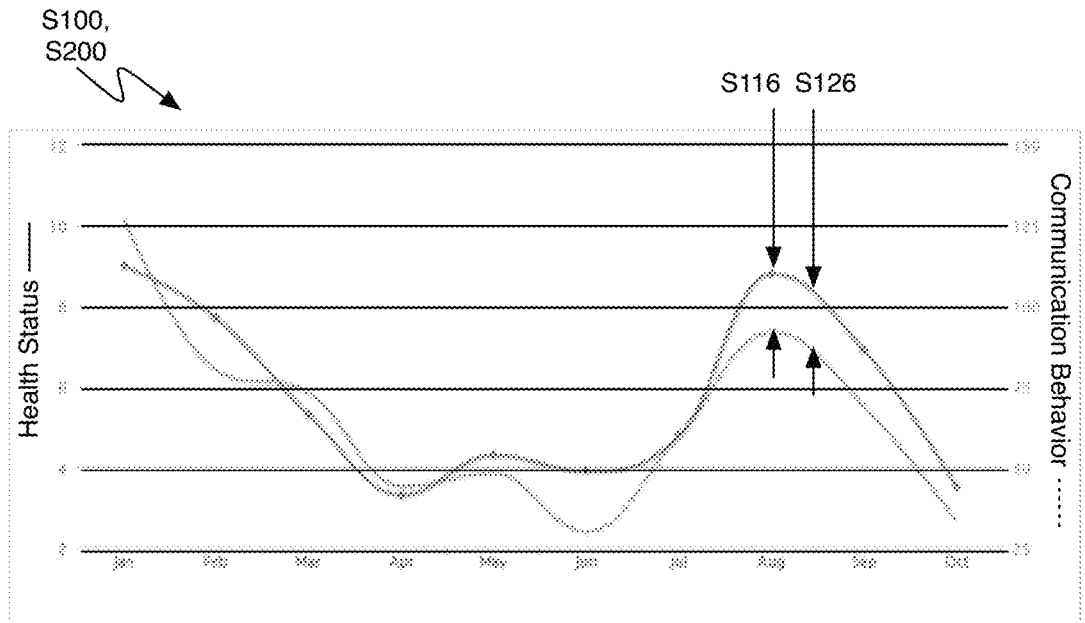
FIG. 4 is a graphical representation of variations in accordance with the first and second methods.

In one implementation, Block S116 characterizes patient-provided treatment adherence data from the first survey and associates the treatment adherence characterization with the communication behavior characterization from Block S110. At a later time when the patient's communication behavior mimics the communication behavior during the first period, the first method S100 can thus anticipate the patient's treatment adherence at the later time to mimic the patient's treatment behavior during the first time period. In one example, Block S116 correlates a log of use of a first set of outgoing voice communications from a phone call application during the first period with conformity to the treatment regimen by the patient, and Block S126 correlates a frequency of a second set of outgoing voice communications within the phone call application with neglect of the treatment regimen by the patient, as shown in FIG. 4, wherein the log of use of the first set of outgoing voice communications is greater than the frequency of the second set of outgoing voice communications.

Block S116 can additionally or alternatively correlate adherence to the treatment regimen and/or patient communication behavior to patient health status, such as presentation of patient symptoms. In one example, Block S116 extracts a patient symptom level from the first survey and presentation of patient symptoms (e.g., how well the patient is feeling) with patient communication behavior (e.g., how, when, and who the patient contacts during a period of time). In this example, Block S116 can determine that a period during which the patient sends a low volume of text messages to a large breadth of contact types and engages in long phone conversations with a limited number of contacts corresponds to minimal symptom presentation, and Block S126 can determine that a period during which the patient sends a low volume of text messages to a low number of unique contacts and engages in short phone conversations with a single contact corresponds to a high degree of symptom presentation. In this example, Block S116 can also correlate minimal symptom presentation with a certain degree of treatment adherence during the first period (e.g., the patient followed the treatment adherence properly), and Block S126 can further correlate higher degree of symptom presentation with a lesser degree of treatment adherence during the second period (e.g., the patient missed a treatment or took an improper dosage).

The first method S100 can repeat elements of Blocks S110, S112, S114, S116, etc. to generate a set of communication behavior-treatment adherence (and health status) features for the patient over time, and these features can be fed into Block S130, Block S160, Block S144, Block S150, Block S172, and/or Block S180, etc. to enable further functionality.

Block S250 of the second method, which recites correlating communication behavior of a patient with health statuses of patients within the subgroup, can implement similar functionality to generate communication behavior-treatment adherence (and health status) features within the subgroup of patients. For example, Block S250 can pair anonymized communication data from various patients exhibiting similar behaviors over time, such as before, during, and after a treatment regime, with survey responses from corresponding patients at corresponding times to output a collection of features specific to the subgroup. Block S250 can thus pass this collection of features to Block S280. Block S280 can thus implement the collection of features to identify trends or patterns between communication behavior, treatment adherence, and presentation of symptoms across the population and generate a corresponding treatment regimen model for the subgroup, as described below.

7. Subgroups

Block S160 of the first method S100 recites selecting a subgroup of a patient population based on the first log of use of the native communication application and a communication behavior common to the subgroup. Generally, Block S160 functions to identify one or more patients within a patient population exhibiting characteristics similar to those of the (current, new, or subsequent) patient, such that subsequent Blocks of the first method S100 can apply preexisting communication behavior data, treatment adherence data, health status data, etc. and corresponding characterizations, patterns, models, etc. of this data to inform and/or improve manipulation of the patient's health-related data.

In one implementation, Block S110 characterizes patient communication behavior prior to beginning a treatment regimen, and Block S160 selects a set of other patients within a patient population who exhibit(ed) similar communication behaviors prior to beginning similar treatment regimens. Block S160 can further select and/or filter the patient population based on a diagnosis, therapy prescription, age, gender, location, and/or other demographic, activity behaviors prior to beginning similar treatment programs, and/or other factors or variables similar to those of the patient. Block S160 can further select the set of other patients and/or update the set of other patients during the patient's treatment regimen based on similar in-treatment communication behaviors (and other behaviors or variables) between the patient and other patients in the patient population.

Block S160 can therefore receive patient communication behavior characterizations of the patient and other patients within the patient population, such as from Block S110 and Block S120, to identify communication behaviors common to the patient and to the subgroup. Block S160 can also select the subgroup as pertinent to the patient based on treatment adherence data and/or trends and/or symptom data and/or trends common to the patient and the subgroup, such as before and/or during a related treatment regimen. Similarly, Block S160 can select the subgroup based on determined relationships between treatment adherence and communication data common to the patient and the other patients within the subgroup.

Block S210 of the second method, which recites identifying a population of patients diagnosed with a health condition, and Block S220, which recites selecting a subgroup of patients within the population exhibiting a similar behavioral characteristic, can implement similar functionality to identify a subset of patients within a patient population that share commonalities, such as one or more diagnoses, health conditions, symptoms, treatment regimens, communication behavior characteristics, treatment adherence characteristics, etc. For example, Block S210 can identify a population of patients prescribed a treatment regimen for a particular diagnosed health condition, such as by identifying anonymized patient profiles tagged with the particular diagnosed health condition, and Block S220 can select a subgroup of patients from the population of patients based on similar communication behavior prior to initiation of the treatment regimen in Block S220. Blocks S230, S240, and S250 can therefore analyze and manipulate communication and/or survey data associated with selected patients within the subgroup (i.e., to estimate treatment regimen adherence, to characterize communication behavior, and to correlate communication behavior and health status of patients, respectively) before and/or after the subgroup is selected in Block S220. However, Blocks S160, S210, and S220 can function in any other way to select a subgroup of related patients from a population of patients.

8. Behavior Feature Engine

Any one or more of the foregoing Blocks of the first and second methods S100, S200 can implement a Behavior Feature Engine (BFE) to handle patient data before, during, and/or following a treatment regimen and to then to manipulate patient data into an effective model.

The BFE includes a collection of statistics—a combination of unique variables or "features"—that vary amongst patients, conditions, and disease states. A subset of features defined in the BFE can thus be implemented to predict the health status of a patient, such as given communication behavior and/or treatment adherence of the patient. The methods can collect raw patient data from the data collection application described above, such as through Block S110, S112, etc. and can then convert this raw data into statistical features to create the BFE, such as on a remote server for a subgroup of patients or locally on a mobile computing device for a particular patient.

For a particular patient, the BFE can extract independent features from one of various types of data or modalities (e.g., phone calls, text messages, instant messages). For example, the BFE can aggregate patient communication data, including a total number of calls made, received, accepted, missed, etc. and a total number of text (e.g., SMS text) messages sent, received, ignored, etc. on a particular day or within another period of time, as shown in FIG. 1A. From this data, the BFE can estimate an interaction balance for the patient, such as by calculating a ratio of incoming communications (e.g., phone calls and text messages) to total communication within a period of time, as well as a patient responsiveness, such as by calculating a number of "missed" interactions within the time frame based on a number of calls not accepted or text messages ignored by the patient with the period of time.

The BFE can also calculate patient interaction diversity, including a total number of individuals with whom the patient interacts, such as through a voice communication application or text messaging application, within the period of time. The BFE can further extract a patient mobility from patient location data, including an approximation of total patient movement during a particular phone call or during the total of a corresponding period of time, such as based on an estimated distance traveled by foot or bike (excluding a distance traveled by car, train, etc.) based on GPS location data of the patient's mobile computing device (e.g., smartphone). The BFE can then generate a mobility radius factor—defining an approximate radius of an imaginary circle encompassing locations visited by a patient within a period of time—and tag or associate patient communication data with this mobility radius factor.

The BFE can also calculate other location data features, such as time spent at home, time spent at work, transition between home/work/social locations, isolation at a particular location for extended periods of time, unpredictability (i.e., entropy) in location information, etc. The BFE can also implement mobile phone usage, such as screen unlocks and application usage, to calculate features that summarize variations and periods of patient activity and inactivity, identify extended periods during which the patient is hyperactive on the device, and/or determine sleep patterns.

The BFE can further handle other types of patient data. For example, the BFE can estimate an amount of physical activity undertaken by the patient within the period of time based on motion sensor (e.g., accelerometer) data recorded on the patient's mobile computing device or wearable device, as shown in FIG. 1B. In this example, the BFE can also implement machine learning, such as feature extraction or pattern matching, to correlate motion data with a particular type of action, such as walking, playing tennis, or eating. The BFE can then associate communication data (e.g., times and types) with the activity data, such as an amount of time the patient spent in phone calls during an activity, set of activities, or period of time including one or more particular activities. However, the BFE can handle, manipulate, and/or aggregate any other type of patient data, such as any of the data collected as described above.

The BFE can segment patient behavior to enable identification of patient behavioral patterns. For example, the BFE can segment patient data according to any suitable period of time or time frame, such as by whole day, a preset number of hours, daytime and nighttime, weekdays and weekends, months, etc., and thus extrapolate an hourly, daily, weekly, or other time-dependent behavioral pattern. The BFE can similarly segment patient behavior data by patient location, such as home, office, etc., and thus identify location-related patient behavioral patterns.

Feature extraction of patient data within the BFE can be driven by predefined metrics, such as distinctness, aggregation, entropy, or percentage change over time for a particular patient, and the BFE can group such features by time, patient, patient subgroup, etc. Features can be stored as standalone features or, as behavior changes, features generated through comparison of two or more standalone features from different times (or across a group or in comparison to a baseline feature). The BFE can then extract a time-dependent behavior pattern for a patient or a subgroup of patients from these features. For example, the BFE can identify and measure statistically significant changes in patient behavior throughout a treatment, including before, during, and/or after administration of the treatment (e.g., a pharmacological treatment, physical therapy, etc.).

The BFE can also generate comparative representations of base patient behavior features. For example, the BFE can compare a patient behavior feature value for a specific period of time against any one or more of a baseline (i.e., typical or normal) behavior for the patient as indicated by patient data gathered over time, historical patient behavior data (e.g., at a similar times of day or days of a week), an expected or healthy behavior as suggested by an expert, healthcare professional, literature, a past study, and/or an average or common behavior observed in patient population or patient subgroup exhibiting behaviors similar to the those of the patient. The BFE can output such comparative representations in the form of differences, ratios, percentages, etc. and can handle the comparative representations as discrete features.

9. Predictive Modeling Engine

Blocks S130, S280, S284 of the first and second methods S100, S200 recite generating models based on communication and survey data of one or more patients. Generally, Blocks of the first and second methods S100, S200 can implement the BFE in conjunction with a Predictive Modeling Engine (PME) to generate patient-, patient subgroup-, and/or treatment-specific models.

Generally, the PME functions to identify and measure statistically significant changes in patient behavior through periods of varied symptom presentation or throughout a treatment, including before, during, and/or after administration of the treatment (e.g., a pharmacological treatment, physical therapy, etc.), to generate a (patient- or subgroup-level) predictive model accordingly, and to train the predictive model with additional patient data over time. The PME can identify correlations between patient behavior(s), symptoms, treatment adherence, and other features extracted in the BFE to transform a large amount of patient data into a predictive model defining links between such observed patient data and associated efficacy, mitigation, abatement of patient symptoms and/or health condition via one or more treatments (i.e., therapies), patient wellness, quality of life, and/or general health of the patient.

The PME can therefore implement patient communication data to construct a patient behavior model from multiple patient-related features, such as including total call duration over a period of time (e.g., for a day, for a week), proportion of time spent on calls on weekdays and weekends (or days and nights), number of unique contacts in communication with the patient, and percentage change in patient communication with certain contacts over a baseline period of time. The PME can also associate such features—relative to the baseline—with patient treatment adherence, symptom presentation, and health condition progression to generate a holistic patient- or subgroup-specific treatment model.

In one example, the PME generates a model including a derived link between patient health status and patient behavior features extracted in the BFE by identifying and measuring statistically significant changes in behavior during days characterized by enhanced patient symptoms and days characterized by relatively normal patient symptoms for an individual patient or across a patient population subgroup. In this example, the PME can identify a correlation between low patient activity and enhanced symptoms and generate a predictive model accordingly. Such data can be applied to a particular patient, a patient subgroup, and/or a patient population to quantify how effectively a treatment enables a patient to be more active and return to a normal work-life balance in comparison to an alternative treatment. In another example, the PME analyzes behavior data of a bipolar patient to correlate patient behaviors with patient symptoms. In this example, the PME and BFE can cooperate to identify baseline patient communication behavior and associate this with a normal patient state, identify a period of low patient activity and isolated communication behavior and associate this with a depressive episode, and identify a period of patient hyper-activity, long work hours, and a high degree of socializing and associate this with a manic episode. The PME can thus generate a patient-specific model relating patient behavior with normal, manic, and depressive states. The PME can therefore manipulate changes in patient activity or behavior, work, work-life balance, productivity, stress and anxiety, health and wellness, treatment outcome (e.g., self-reported by the patient or entered by a caregiver, family-member, provider, employer, etc.), etc. to identify correlations between patient behavior and patient health and build predictive models based on behavior change, treatment adherence, symptom presentation, and/or treatment outcome patterns.

As described above, the PME can implement machine learning, data mining, and/or statistical approaches to generate one or more models specific to a patient, a patient subgroup, or a patient population. In particular, the PME can apply statistical approaches to inform an understanding of underlying patient behavioral data through distributions, correlations, hypothesis testing, etc. by pairing original features extraction within the BFE with clinical insight and domain-specific intuition, such as from a doctor, nurse, pharmacist, etc. The PME can apply feature selection approaches to determine a most predictive subset of features. For example, the PME can implement correlation-based feature selection (CFS), minimum redundancy maximum relevance (mRMR), Relief-F, symmetrical uncertainty, information gain, or other statistical methods and statistic fitting techniques to select a set of features output from the BFE. The PME can also implement support vector machines, ensemble learning (e.g., boosting, random forest), logistic regression, Bayesian learning (e.g., wherein an outcome variable is a predefined class or category), or other machine learning techniques to predict patient behavior, symptoms, treatment outcome, etc. In certain cases, additional complexity can be added to this process. For example, the PME can implement cost-sensitive learning and sampling approaches when distribution of data between categories or classes is unequal, such as when a symptom of interest is depression, which is detectable within a patient on fewer than 10% of total days of a patient study.

Figure 5:
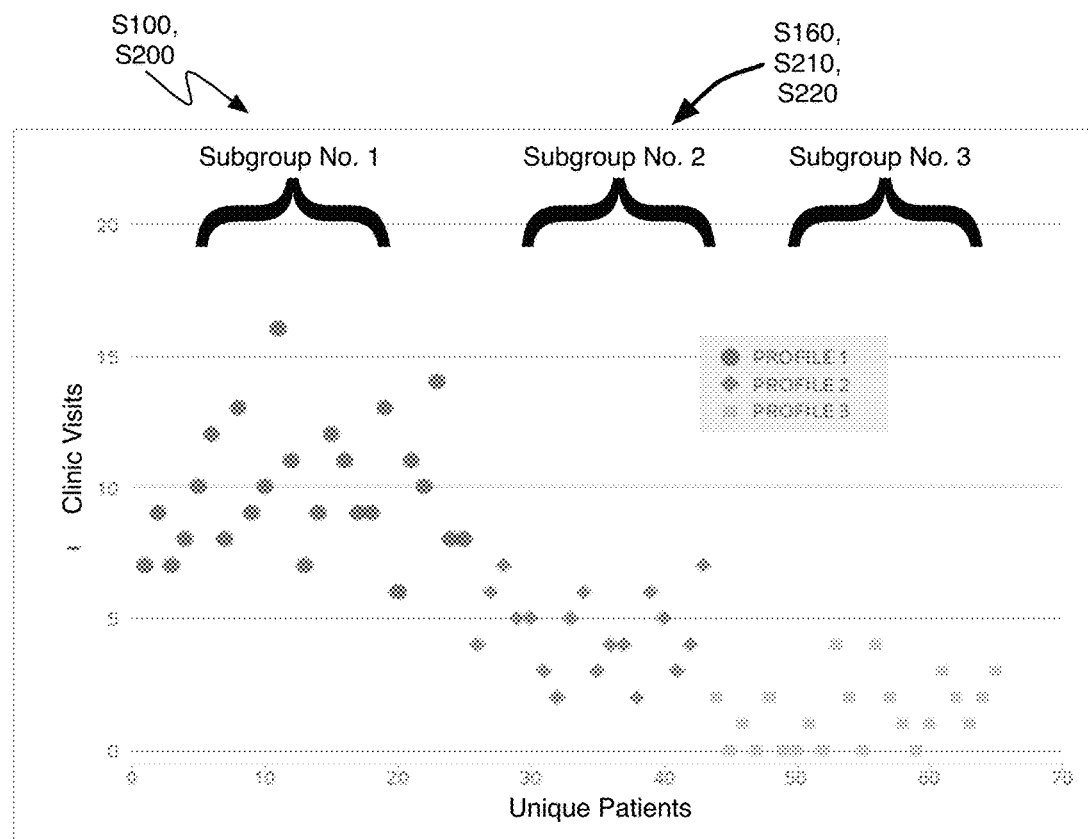
FIG. 5 is a graphical representation of variations in accordance with the first and second methods.

In one implementation, the PME applies regression approaches and generalized linear models for model outputs that include continuous values, such as prediction of symptom severity. In another implementation, the PME applies Support Vector Machine (SVM) classification approaches for model outputs that include discrete values, such as for patient health risk prediction. In another implementation, the PME applies clustering techniques for model outputs that include a set of undefined clusters, such as a centroid-based, density-based, connectivity-based, and/or a distribution-based approach to define a cluster based on patient behaviors, as shown in FIG. 5. For example, the PME can apply clustering techniques for a model output that specifies a group of patients with similar symptoms or behaviors together. The PME can apply similar techniques to detect anomalies and/or outliers in aberrant cases in collected data, such as patients within a population who do not respond to a treatment or show adverse effects uncharacteristic of the greater patient population. The PME can further train a linear model by fitting a line to collected data or features, and the PME can train a Bayesian network classification model and/or a Gaussian mixture classification model through Expectation-Maximization.

The PME can additionally or alternatively model subgroups of patients with a population of patients. In one implementation, the PME identifies a subset (i.e., subgroup) of patients with a certain degree of similarity with one subset of patients in the population and a certain degree of dissimilarity with another subset of patients in the population, such as with respect to one or more behaviors. For example, for a particular therapy, the PME can select a first subgroup of patients who become more active during the therapy and a second subgroup—exclusive of the first subgroup—of patients who show little marked behavior change during the therapy. In this example, the PME can also assign different intervention triggers, reminder types, notification triggers, etc. to each of the first and second subgroups. The PME can therefore apply behavior data passively collected from a patient population to identify clusters of related patients within the population, as shown in FIG. 5.

As described above, the PME can generate models that output predicted patient treatment adherence, patient symptom presentation, treatment efficacy, patient response to a treatment, etc. However, the PME can generate models that additionally or alternatively incorporate or output one or more of a risk of admission or re-admission to an associated care provider, risk of a pending emergency room visit, risk of retrogression of clinical symptoms, etc. A model generated through the PME can therefore support or enable early detection of higher-risk patients, prediction of patient hospitalization or symptom relapse, and timely patient intervention and messaging to improve or change patient behaviors.

The PME can further train or update a model over time, such as when new data from a specific patient or anonymized data from a patient subgroup becomes available. For example, the PME can verify a previous prediction outcome model for a specific patient in response to receiving feedback from the patients. Alternatively, the PME associates the patient with an alternative subgroup and selects an alternative model for the patient, accordingly, based on new patient feedback.

10. Health Risk Identification

Block S232 of the second method S200 of the method recites identifying a relationship between communication behaviors of patients within the subgroup, characteristics of medical symptoms of patients within the subgroup, and a treatment regimen administered to patients within the subgroup. Block S280 of the second method S200 further recites generating a health risk model for the subgroup based on the relationship, the health risk model defining a correlation between a change in communication behavior and risk of change in a medical symptom.

In this implementation of the first method, an individual patient and can be diagnosed or at-risk for a certain condition, and Blocks of the first method can therefore estimate symptom severity, health status, or health risk change] for the patient based on volunteered survey results and/or an applicable health risk model for a corresponding subgroup of patients. Generally, the first method S100 can implement the health risk model generated in the second method S200 to predict a health risk of an individual patient. In particular, Block S162 of the first method can retrieve the health risk model associated with the subgroup (and defining a correlation between risk of change in a medical symptom and communication behavior for patients within the subgroup), and Block S172 can predict a risk of change in a medical symptom for the patient based on the log of use of the native communication application and the health risk model.

Blocks of the methods can therefore extract patient symptom severity or health status over time from corresponding survey responses collected in corresponding Blocks of the methods (e.g., Blocks S112, S122, etc.). For example, a survey delivered to a patient can include an explicit inquiry into if and when a symptom occurred and a severity of symptom presentation, and Block S114 can analyze the patient's response to the survey to determine if and/or to what extent the patient symptoms presented for the corresponding time period. Block S114 can subsequently pass the degree of symptom severity to Block S116. Block S124, Block S230, etc. can implement similar functionality to deliver and assess patient surveys.

Block S116 (and Block S126, etc.) can subsequently define a relationship between a degree of symptom severity or health status and a quality and/or quantity of communication (i.e., communication behavior, location behavior, and/or phone usage behavior) of the patient for a corresponding period of time. Block S116 can then pass this relationship to Block S172 to predict symptom severity or health status for the patient and/or for other patients in a corresponding subgroup.

In one implementation, Block S116 characterizes patient-provided symptom severity and health status data from the first survey and associates this characterization with the communication behavior characterization from Block S110. At a later time when the patient's communication behavior mimics the communication behavior during the first period, the first method S100 can thus anticipate the patient's symptom severity and health status at the later time to mimic the patient's treatment behavior during a corresponding time period. In one example, Block S116 correlates a frequency of a first set of outgoing voice communications from a phone call application during the first period with high symptom severity for the patient, and Block S126 correlates a frequency of a second set of outgoing voice communications within the phone call application with low symptom severity for the patient, wherein the frequency of the first set of outgoing voice communications is greater than the frequency of the second set of outgoing voice communications.

Block S116 can additionally or alternatively correlate patient symptom severity or health status and/or patient communication behavior to a change in healthcare utilization, such as readmission or increased hospital visits. In one example, Block S116 extracts a patient symptom severity from the first survey and presentation of patient symptoms (e.g., how well the patient is feeling) with patient communication behavior (e.g., how, when, and who the patient contacts during a period of time). In this example, Block S116 can determine that a period during which the patient sends a low volume of text messages to a large breadth of contact types and engages in long phone conversations with a limited number of contacts corresponds to low symptom severity, and Block S126 can determine that a period during which the patient sends a low volume of text messages to a low number of unique contacts and engages in short phone conversations with a single contact corresponds to a high symptom severity. In this example, Block S116 can also correlate low symptom severity with a certain amount or pattern of healthcare utilization during the first period (e.g., the patient did not have to visit the doctor for anything other than regular checkups), and Block S126 can further correlate high symptom severity with increased healthcare utilization during the second period (e.g., the patient had to visit the doctor several times beyond the regular visits).

The first method S100 can repeat elements of Blocks S110, S112, S114, S116, etc. to generate a set of communication behavior-symptom severity (and health status) features for the patient over time, and these features can be fed into Block S130, Block S160, Block S162, Block S144, Block S150, Block S172, and/or Block S180, etc. to enable further functionality.

Block S232 of the second method S200, which recites identifying a relationship between communication behaviors of patients within the subgroup, characteristics of medical symptoms of patients within the subgroup, and a treatment regimen administered to patients within the subgroup, can implement similar functionality to generate communication behavior-symptom severity (and health status) features within the subgroup of patients. For example, Block S232 can pair anonymized communication data from various patients exhibiting similar behaviors over time, such as while presenting low or high symptom severities, with survey responses from corresponding patients at corresponding times to output a collection of features specific to the subgroup. Block S232 can thus pass this collection of features to Block S280

In one implementation, Block S280 applies the collection of features to identify trends or patterns between communication behavior, symptom severity, and healthcare utilization across the population and generates a corresponding intervention plan for the subgroup, as described below.

11. Health Risk Model

As described above, Blocks of the first and second methods S100, S200 can implement the PME to generate patient- and/or subgroup-specific models.

In particular, Block S, which recites generating a health risk model including the first log (e.g., frequency) of use of the native communication application, the second log of use of the native communication application, the first symptom severity or health status, and the second symptom severity or health status, can implement the PME to generate a model linking patient communication behavior and health risk (e.g., symptom severity, risk of relapse, risk of hospital readmission, health status, etc.). For example, Block S130 can implement the BFE to determine that low communication periods commonly follow periods in which the patient correlates with high symptom severity and that period characterized by relatively high levels of patient activity correspond to low symptom severity. In this example, Block S130 can then implement the PME to generate a corresponding model specific to the patient. Block S130 can subsequently pass this model to Block S144 to estimate a subsequent patient health risk at a subsequent time based on patient behavior at the subsequent time. In particular, in this example, Block S144 can determine that the patient is at a high risk for increased symptom severity if the patient's behavior (e.g., communication behavior and/or activity level) substantially matches recorded patient behavior associated with that symptom severity (as defined by the health risk model).

Block S162, which can recite retrieving a health risk model associated with the subgroup, can select a preexisting health risk (or risk identification) model—generated by the PME and associated with a subgroup of patients—based on selection of the subgroup in Block S160. Block S144 can similarly function to pass subsequent patient behavior data into the health risk model to predict a subsequent level of patient risk for presenting symptom greater than a threshold severity. In this variation of the first method, Block S172 can additionally or alternatively predict short-term and/or long-term patient risk for high symptom severity or change in health status or disease progression, such as based on a change in communication behavior of the patient over a certain time period. For example, if the patient's total communications increase during a certain time period and this increase in communications is common for patients within the subgroup who show a decrease in symptom severity—as defined in the health risk model—Block S172 can predict that the patient will exhibit a similar decrease in symptom severity.

However, Block S130 and Block S160 can function in any other way to generate and retrieve a predictive model defining a relationship between symptom severity or health status and patient communication behavior over time, respectively.

Block S172 can further estimate an efficacy of the patient intervention (e.g., nurse outreach, doctor-patient communication, automated health tips delivered through the patient's mobile computing device) in improving the health condition of the patient according to a comparison between changes in symptom severity or health status of the patient. Block S172 can therefore implement elements of the BFE and/or the PME to predict the outcome of the intervention for the patient. For example, Block S172 can identify a pattern of communication behavior of the patient, correlate the pattern of communication behavior with intervention outcomes, and then compare the interventions (e.g., based on symptom presentation recorded in various survey responses entered by the patient) to changes in healthcare utilization. In this example, if the patient is delivered relevant interventions but shows worsening or unchanged symptoms, Block S172 can estimate a low efficacy of the intervention in treating the patient's condition. Furthermore, in this example, Block S172 can compare the patient to existing health condition data and/or a health risk model for a subgroup of patients to determine if worsening symptoms despite delivering interventions is common or expected for the patient's diagnosed health condition and/or for similar patients (i.e., patients within the subgroup). Block S172 can thus predict the efficacy of the interventions accordingly.

Block S260 of the second method S200 similarly recites estimating an efficacy of the interventions in improving the health condition for patients within the subgroup based on of the delivery of interventions to patients within the subgroup. Generally, Block S260 implements techniques similar to Block S172 to apply elements of the BFE and/or the PME to predict the outcome of the interventions for the subgroup of patients within a patient population. For example, for patients within the selected subgroup, Block S260 can identify an increase in use of native communication applications by patients from prior to initiation of the interventions to the patients to during and after delivery of the interventions to the patients, correlating the increase in use of the native communication applications by the patients with improved health status of the patients, and correlating improved health status of the patients with efficacy of the interventions in improving the health condition of patients within the subgroups. In this example, Block S260 can apply survey response and communication behavior of patients within the subgroup—and a known health condition common to patients within the subgroup—to predict the efficacy of a nurse outreach program in providing support for mental health issues of patients within the subgroup. Additionally or alternatively, Block S260 can implement such patient data to estimate the efficacy of a health tips program in improving health-related behaviors of diabetic patients within the subgroup.

In one implementation, block S172 and Block S260 output quantitative values of intervention efficacy for the patient and the patient subgroup, respectively. For example, Block S172 can output a predicted intervention efficacy of 80%, indicating that four out of five similar patients show a reduction in symptom severity or an improvement in health status. As in this example, Block S172 can additionally output a confidence interval indicating a statistical confidence in the intervention regimen, which can be dependent on a size of a patient subgroup associated with an intervention efficacy model used to estimate treatment efficacy for the patient or dependent on a predicted accuracy and/or availability of patient communication and survey response data, as shown in FIGS. 1A and 1C.

Alternatively, Block S172 and Block S260 output binary indicators of intervention efficacy. For example, if predicted intervention efficacy falls below a threshold, such as below a 70% predicted improvement rate, Block S172 and/or Block S260 can output a negative indicator of intervention efficacy. In response to a negative predicted intervention efficacy, Block S172 can prompt Block S180 to automatically trigger a notification to care providers suggesting that a different intervention plan might better serve the patient. If data regarding past intervention successes is available modification of the treatment regimen or prompt a care provider to modify the existing treatment regimen or to prescribe a new treatment regimen for the patient, as described below. Similarly, in response to a negative predicted treatment efficacy, Block S260 can prompt Block S284 to implement similar functionality to automatically modify or prompt manual modification of the treatment regimen for the subgroup of patients.

As shown in FIG. 1C, one variation of the first method S100 includes Block S180, which recites generating an updated intervention regimen according to the efficacy of the intervention regimen. Generally, Block S180 functions to modify an intervention plan based on an intervention efficacy prediction output in Block S172. In one example, if the patient's symptoms worsen over time when improvement is expected despite delivering relevant interventions, Block S180 can prompt a doctor, pharmacologist, etc. to prescribe an alternative intervention program.

As shown in FIG. 2B, Block S284 of one variation of the second method S200 similarly recites updating the intervention regimen for patients within the subgroup and currently prescribed the intervention regimen in accordance with the intervention efficacy predicted in Block S260.

In one implementation of Block S284, the second method S200 characterizes communication behavior of a patient following diagnosis of a medical condition and before administration of an intervention program, applies the characterized communication behavior to select a subgroup of patients with similar diagnoses and communication behaviors prior to administration of intervention programs, and selects an intervention program for the patient based on a predicted efficacy of the intervention for the patient, which is informed by an actual efficacy of the intervention within the selected subgroup (and/or a corresponding intervention efficacy model for the subgroup, as described above). Block S284 can function to pair a new patient to a subgroup of current and/or previous patients and to automatically prescribe an intervention regimen to the new patient accordingly.

12. Adherence Model

As described above, Blocks of the first and second methods S100, S200 can implement the PME to generate patient- and/or subgroup-specific models.

In particular, Block S130, which recites generating a patient regimen adherence model including the first log of use of the native communication application, the second log of use of the native communication application, the first adherence, and the second adherence, can implement the PME to generate a model linking patient communication behavior and treatment adherence. For example, Block S130 can implement the BFE to determine that low communication periods commonly follow periods in which the patient diverts from a prescribed treatment regimen and that period characterized by relatively high levels of patient activity correspond to suitable adherence to the treatment regimen. In this example, Block S130 can then implement the PME to generate a corresponding model specific to the patient. Block S130 can subsequently pass this model to Block S144 to estimate a subsequent patient treatment adherence at a subsequent time based on patient behavior at the subsequent time. In particular, in this example, Block S144 can determine that the patient has effectively complied with his prescribed treatment program if the patient's behavior (e.g., communication behavior and/or activity level) substantially matches recorded patient behavior associated with treatment adherence compliance (as defined by the patient treatment adherence model), and Block S144 can determine that patient has not suitably complied with his prescribed treatment program when the patient's behavior substantially matches recorded patient behavior associated with treatment adherence neglect.

In this foregoing implementation, Block S144, which recites estimating a third adherence within the third time period based on the patient regimen adherence model and the third log of use of the native communication application, functions to pass data from a subsequent third period of time into the adherence model generated in Block S130 to predict patient adherence to the treatment regimen during the third period of time. Block S144 can additionally or alternatively estimate a patient response to a most-recent administration of the treatment program, such as based on a patient response component of the treatment adherence model.

Alternatively, Block S162, which recites retrieving a regimen adherence model associated with the subgroup, can select a preexisting treatment adherence model—generated by the PME and associated with a subgroup of patients—based on selection of the subgroup in Block S160. Block S144 can similarly function to pass subsequent patient behavior data into the regimen adherence model to predict a subsequent level of patient adherence to a prescribed treatment. In this variation of the first method, Block S172 can additionally or alternatively predict short-term and/or long-term patient response to the treatment, such as based on a change in communication behavior of the patient soon after beginning a treatment program. For example, if the patient's total communications increase soon after beginning a treatment regimen for a particular condition and this increase in communications is common for patients within the subgroup who positively respond to the treatment regimen—as defined in the regimen adherence model—Block S172 can predict that the patient will exhibit a similar positive response to the treatment regimen. Block S172 can similarly predict patient satisfaction in the treatment regimen based on data of other patients within the subgroup and the regimen adherence model.

However, Block S130 and Block S160 can function in any other way to generate and retrieve a predictive model defining a relationship between treatment regimen adherence and patient communication behavior over time, respectively.

13. Treatment Regimen Model

As shown in FIG. 2B, one variation of the second method S200 includes Block S280, which recites generating a treatment regimen model for the subgroup, the treatment regimen model defining a correlation between communication behavior, treatment responses, and treatment regimen outcomes for patients within the subgroup. Generally, Block S280 can implement the PME to generate a model correlating patient behavior to patient treatment outcome for a subgroup of patients. In one example, Block 242 can implement behavior data of a subsequent patient to match the subsequent patient to the subgroup, and Block S282 can feed behavior data of the subsequent patient into the corresponding treatment regimen model to generate a predicted treatment regimen outcome for the subsequent patient following administration of the treatment regimen as shown in FIG. 2B. Block S282 can similarly predict a health condition relapse risk for the subsequent patient based on the treatment regimen model, such as for the treatment regimen model that includes a relapse risk output component.

In one implementation, Block S280 implements the PME to generate a treatment regimen model for the subgroup based on adherence to the treatment regimen, communication behavior, and survey responses of patients within the subgroup throughout a period of time. For example, Block S280 can implement the PME to generate the treatment regimen model for the subgroup by identifying patterns in communication behavior during administration of the treatment regimen and correlating patterns in communication behavior with treatment responses of patients within the subgroup. In this implementation, Block S282 can thus feed any one or more of adherence to the treatment regimen, communication behavior, and a survey response of a subsequent patient into the treatment regimen model to output a predicted effect of the associated treatment on the subsequent patient, such as for a particular period of time during administration of the treatment program to the subsequent patient.

However, Block S280 can function in any other way to generate a predictive model defining a relationship between treatment outcome for a patient and patient communication behavior over time.

14. Treatment Efficacy Model

Block S172, which recites estimating an efficacy of the treatment regimen in treating the health condition of the patient according to a comparison between the treatment response and the adherence to the treatment regimen by the patient, functions to implements elements of the BFE and/or the PME to predict the outcome of the treatment regimen for the patient. For example, Block S172 can identify a pattern of communication behavior of the patient, correlate the pattern of communication behavior with a pattern of treatment adherence, and then compare the pattern of treatment adherence to a trend in patient treatment response (e.g., based on symptom presentation recorded in various survey responses entered by the patient). In this example, if the patient exhibits strong treatment adherence but worsening symptoms, Block S172 can estimate a low efficacy of the treatment in treating the patient's condition. Furthermore, in this example, Block S172 can compare the patient to existing health condition data and/or a treatment outcome model for a subgroup of patients to determine if worsening symptoms despite strong treatment adherence is common or expected for the patient's diagnosed health condition and/or for similar patients (i.e., patients within the subgroup). Block S172 can thus predict the efficacy of the treatment accordingly.

Block S260 of the second method S200 similarly recites estimating an efficacy of the treatment regimen in treating the health condition for patients within the subgroup based on adherence to prescribed treatment regimens and health statuses of patients within the subgroup. Generally, Block S260 implements techniques similar to Block S172 to apply elements of the BFE and/or the PME to predict the outcome of the treatment regimen for the subgroup of patients within a patient population. For example, for patients within the selected subgroup, Block S260 can identify an increase in use of native communication applications by patients from prior to initiation of the treatment regimen by the patients to during administration of the treatment regimen by the patients, correlating the increase in use of the native communication applications by the patients with improved health status (e.g., increased wellness, reduced symptoms) of the patients, and correlating improved health status of the patients with efficacy of the treatment in treating the health condition of patients within the subgroups. In this example, Block S260 can apply survey response and communication behavior of patients within the subgroup—and a known health condition common to patients within the subgroup—to predict an efficacy of a physical therapy regimen in treating physical handicaps for patients within the subgroup. Additionally or alternatively, Block S260 can implement such patient data to estimate the efficacy of a pharmacotherapy regimen in treating mental disorders for patients within the subgroup.

In one implementation, Block S172 and Block S260 output quantitative values—from a scale or spectrum of treatment values—of treatment efficacy for the patient and the patient subgroup, respectively. For example, Block S172 can output a predicted treatment efficacy of 80%, indicating that four out of five similar patients recover from a diagnosed condition following the corresponding treatment regimen. As in this example, Block S172 can additionally output a confidence interval indicating a statistical confidence in the predicted treatment regimen, which can be dependent on a size of a patient subgroup associated with a treatment efficacy model used to estimate treatment efficacy for the patient or dependent on a predicted accuracy and/or availability of patient communication and survey response data, as shown in FIGS. 1A and 1C.

Alternatively, Block S172 and Block S260 output binary indicators of treatment efficacy. For example, if predicted treatment efficacy falls below a threshold efficacy, such as below a 70% predicted success rate, Block S172 and/or Block S260 can output a negative indicator of treatment efficacy. In response to a negative predicted treatment efficacy, Block S172 can prompt Block S180 to automatically trigger modification of the treatment regimen or prompt a care provider to modify the existing treatment regimen or to prescribe a new treatment regimen for the patient, as described below. Similarly, in response to a negative predicted treatment efficacy, Block S260 can prompt Block S284 to implement similar functionality to automatically modify or prompt manual modification of the treatment regimen for the subgroup of patients.

As shown in FIG. 1C, one variation of the first method S100 includes Block S180, which recites generating an updated treatment regimen according to the efficacy of the treatment regimen. Generally, Block S180 functions to modify a treatment prescription based on a treatment efficacy prediction output in Block S172. In one example, if the patient exhibits improved symptoms when a medication dosage is skipped or inadvertently reduced by the patient (or care giver, etc.), Block S180 can respond to such improved symptoms by modifying the prescribed medication dosage specified in the treatment regimen for the patient, as shown in FIG. 1C. In another example, if the patient's symptoms worsen over time when improvement is expected despite strong patient adherence to the treatment program, Block S180 can cancel the current treatment program and prescribe an alternative automatically or prompt a doctor, pharmacologist, etc. to prescribe an alternative treatment program.

As shown in FIG. 2B, Block S284 of one variation of the second method S200 similarly recites updating the treatment regimen for patients within the subgroup and currently prescribed the treatment regimen in accordance with the treatment efficacy predicted in Block S260.

In one implementation of Block S284, the second method S200 characterizes communication behavior of a patient following diagnosis of a medical condition and before administration of a treatment program, applies the characterized communication behavior to select a subgroup of patients with similar diagnoses and communication behaviors prior to administration of treatment programs, and selects a treatment program for the patient based on a predicted efficacy of the treatment for the patient, which is informed by an actual efficacy of the treatment within the selected subgroup (and/or a corresponding treatment efficacy model for the subgroup, as described above). For example, Block S282 can prescribe a custom medication and custom dosage for the patient based on the predicted treatment regimen outcome for the patient, such as by passing different medications and/or dosages into the subgroup regimen outcome model and selecting a particular medication and/or dosage that yields a highest predicted treatment efficacy. Therefore, Block S284 can function to pair a new patient to a subgroup of current and/or previous patients and to automatically prescribe a treatment regimen to the new patient accordingly.

15. Notifications

Block S150 of the first method S100 recites presenting a treatment-related notification based on the third adherence through the mobile computing device. Generally, Block S150 functions to generate and present a notification to the patient through the patient's mobile computing device to provide guidance to the patient during the treatment program, such as in the form of a reminder to perform a particular task (shown in FIG. 1A), suggest or enforce a behavior change, provide positive reinforcement for a behavior, provide behavioral insights, or share a patient symptom and/or behavior timeline. For example, once Block S144 identifies a period of low treatment adherence or treatment neglect, Block S150 can generate a notification including a reminder to take a prescribed medication and transmit the reminder to the patient's mobile computing device, wherein a native application executing on the mobile computing device displays the notification, such as in the form of a pop-up notification. Block S150 can transmit the notification to the mobile computing device for display at a prescribed treatment administration time, such as a 9 AM and 5 PM—dosage times prescribed by a doctor—on a day following estimated treatment program neglect by the patient. Alternatively, Block S150 can transmit the notification to the patient's mobile computing device substantially in real time in response to a patient action, inaction, behavior, or behavior change. For example, Block S150 can generate a notification reciting "everything all right?" and transmit the notification to the patient in response to a detected abrupt change in a patient behavior pattern (e.g., the patient calls the same family member every morning at 9 AM, but 9:15 AM passes on a present day without an outgoing or incoming phone call).

Block S150 can also incorporate additional patient information in the notification. For example, Block S150 can generate a notification that specifies a medication dosage for the patient, such as including how many pills of a certain type (or size, shape, color, etc.). In this example, the notification can incorporate dosage information based on an updated treatment regimen, such as output in Block S180. Block S150 can additionally or alternatively generate the notification that includes past patient data indicating an expected outcome if the patient adheres to the treatment regimen and/or an expected outcome if the patient neglects the treatment regimen, such as based on a patient or subgroup treatment adherence model.

Figure 3:
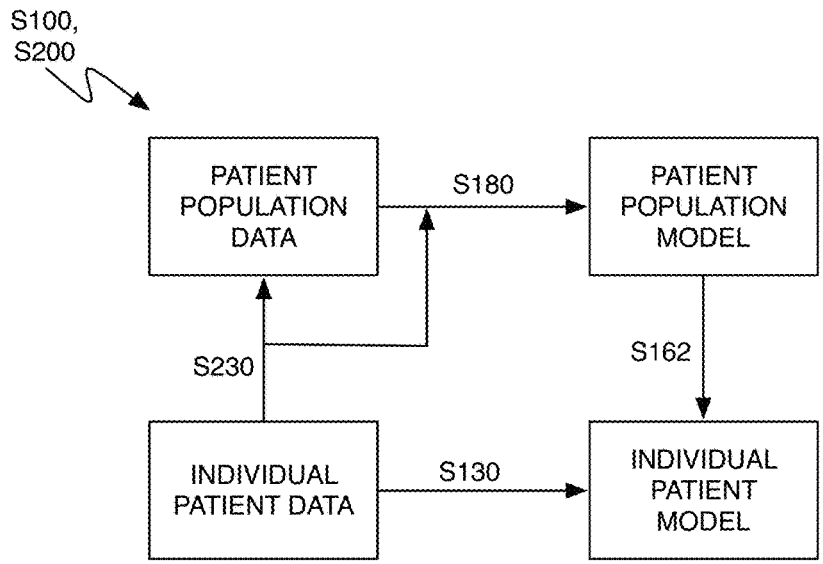
FIG. 3 is a flowchart representation of variations in accordance with the first and second methods.

Block S150 can generate the notification that includes a prompt requesting confirmation of patient implementation of the action item specified in the notification (e.g., the patient took his prescribed medication). For example, the notification can recite "It's time to take your meds" and include input regions reciting "Roger that!" and "Remind me later," as shown in FIG. 1A. Block S150 can subsequently pass a "Roger that!" selection back into the treatment adherence model of the patient as adherence to the treatment program, and Block S150 can pass a "Remind me later" selection into the treatment adherence model as neglect or delay of the treatment program, as shown in FIG. 3.

Block S150 can additionally or alternatively interface with a care provider, such as a nurse or doctor (e.g., through a care provider interface executing on a corresponding computing device), to generate a custom notification. For example, Block S150 can transmit or share patient information, including health condition, treatment regimen, actual and estimated patient adherence, survey response, and/or actual and estimated treatment response data of the patient, with the care provider and guide the care provider in identifying a patient problem or need. Block S150 can then receive from the care provider a selection for a default notification from a pre-populated list of available and/or applicable default notifications. Alternatively, Block S150 can prompt the care provider to enter a custom textual and/or image-based (e.g., infographic) notification for the patient and then pass the notification back to the patient. In one example, Block S172 predicts a risk of change in a medical symptom for the patient based on a risk of increased symptom severity for symptoms associated with a particular disease associated with (e.g., diagnosed in) the selected subgroup, and Block S150 transmits the notification to the care provider if to the risk of change in the medical symptom for the patient exceeds a threshold risk specific to the particular disease, such as a 70% probability that patient symptom severity will systematically increase in the (near) future for a patient diagnosed with diabetes and an 88% probability that patient symptom severity will systematically increase in the (near) future for a patient diagnosed with ADHD.

In addition to generating a reminder for the patient, such as to adhere to a treatment program, Block S150 can additionally or alternatively generate a notification to prompt or reminder the patient to complete a survey, schedule a visit with a doctor or health care provider, to attend a scheduled health-related visit, etc. However, Block S150 can generate a notification including any other information and presented to the patient in any other suitable way or through any other suitable medium.

16. Services

The first and second methods S100, S200 can function to provide one or more services to a care provider associated with a patient and with a subgroup of patients, respectively. In one implementation, the first and second methods S100, S200 support a disease management program by enabling provision of lower cost treatments and/or therapies to patients in exchange for feedback, wherein the first and second methods S100, S200 collect patient feedback as described above. In this implementation, the first method S100 can support tools and one or more mobile applications (i.e., native applications for mobile computing devices) to enable better patient-driven condition management and to reduce symptom flare-ups, and the second method S200 can aggregate and extract valuable information from patient data across a subgroup to support disease management programs by a care provider. For example, the second method S200 can manage or provide analyzed data to a care provider to manage a population with a chronic condition, such as by collecting data about patients outside a clinical setting and generate reports and/or models to aid triage for higher-risk patients, and the first method S100—in conjunction within the second method S200—can support a communication venue or network to enable more effective outreach from a care provider to a patient.

In one example, the first method S100 accesses a second log of use of a native communication application executing on a second mobile computing device by a second patient and predicts a second risk of change in a medical symptom for the second patient based on the second log of use of the native communication application and the health risk model, and Block S150 transmits a scored patient triage list to a care provider (e.g., nurse, hospital, clinic, etc.) according to the risk of change in the medical symptom for the patient and the second risk of change in the medical symptom for the second patient. In another example, Block S150 transmits a notification to the care provider comprises prompting the care provider to schedule a visit with a particular patient.

The first and second methods S100, S200 can therefore target patient interventions to improve patient health and reduce healthcare utilization (e.g., care costs, emergency room visits, pharmaceutical reliance, etc.). For example, the first and second methods S100, S200 can generate and implement models to identify patients at higher-risk for declining health, increased healthcare utilization, and higher hospital readmissions. Once such patients are identified, the first and second methods S100, S200 can prompt a care provider to intervene, thereby initiating targeted care interventions to improve patient health and wellbeing.

The first and second methods S100, S200 can additionally or alternatively extrapolate insights from population-level data to guide care provider improvement in practices, thereby guiding care providers to better patient outcomes. For example, the second method S200 can detect clusters of patients within a population who demonstrate similar behavioral and outcome patterns, identify two clusters of patients who show significantly different readmission rates, identify different treatment practices across the two clusters, and thus guide a care provider in designing a treatment practice based on the readmission rates and the treatment practices across with the two clusters of patients.

In particular, various Blocks of the first and second methods S100, S200 interface with care providers in various ways.

As described above, Block S172 can communicate a predicted (e.g., estimated) efficacy of the treatment regimen for the patient to a healthcare provider associated with the patient. For example, if the predicted efficacy of the treatment falls below a threshold efficacy for the health condition for the patient, Block S172 can transmit an alert or other notification to a doctor, nurse, or other care provider noted in the patient's medical file or recorded as managing treatment of the particular health condition for the patient. In one implementation, Block S172 transmits an alert to a corresponding care provider through a private care provider account accessible through a provider-specific interface (e.g., an online healthcare dashboard), such as a care application logged-in to a care provider's private account and executing on a computing device associated with the care provider. The first method S100 can also enable the care provider to access additional patient information through the care application and/or private care account, such as through an online dashboard. Block S172 can also guide the care provider in modifying an existing treatment program or selecting an alternative treatment program for the patient, as described above, such as by displaying a list of available treatment programs for the patient's health condition in a scored list based on similarities between the patient's behaviors and behavior within a subgroup of patients and treatment efficacies within the subgroup (e.g., via a treatment efficacy model). However, Block S172 can function in any other way to communicate a predicted efficacy of the treatment regimen for the patient to a corresponding care provider.

Block S290 of the second method, which recites transmitting the predicted treatment regimen outcome following administration of the treatment regimen by the subsequent patient to a care provider specified in a digital health profile associated with the subsequent patient, can implement similar techniques and/or methods to share health- and treatment-related information to a care provider related to the (subsequent) patient. For example, Block S290 can transmit a notification including a prompt to respond to a current health status of the subsequent patient to a corresponding care provider. However, Block S290 can function in any other way to communicate a predicted treatment outcome for a patient to a care provider.

Block S270 of the second method, which recites generating a treatment regimen report specific to the subgroup based on the efficacy of the treatment regimen, can implement similar techniques or functionality to communicate a subgroup-wide efficacy report for a particular treatment regimen to a care provider. Generally, Block S270 functions to formulate a report for the efficacy of the treatment regimen with the population based on the estimated efficacy of the treatment regimen output in Block S260. For example, Block S270 can generate the report that includes charts relating patterns in patient symptoms to treatment patterns in treatment adherence, changes in patterns in patient behaviors and survey responses, etc. for within the subgroup over time. In another example, Block S270 generates a treatment report specific to a particular patient within the subgroup, including a predicted risk of health condition decline for the particular patient during administration of the treatment regimen, as shown in FIG. 2A. In this example, Block S270 can thus prompt a care provider to modify a treatment program for a particular patient within a subgroup, such as based on predicted or extrapolated patient risk.

As in Block S172, Block S270 can also guide a care provider in modifying or changing a treatment regimen for the subgroup, such as by identifying and displaying (unexpected) patterns of treatment negligence or patient 'customization' associated with improved patient symptoms and/or patient behaviors within the subgroup. For example, the second method S200 can implement behavior data of patients within the subgroup to compare the wellbeing of the patients and identify those most in need accordingly. Block S270 can thus generate the treatment regimen report that includes a ranking of patients within the subgroup based on need and symptoms. Thus, rather than randomly select patients within a subgroup to contact during the treatment regimen, a nurse practitioner managing dozens of patients can review the treatment report for the subgroup to more effectively triage and determine the patients that are (likely) in need of support. Block S270—and the second method S200 in general—can therefore enable a nurse or other care provider to make real-time decisions and intervene and/or reach out to a particular patient based on real patient data.

However, Block S270 can generate a report that includes any other suitable patient information and can function in any other way to make the report available to one or more care providers, such as related to one or more patients and/or a prescribed treatment regimen for the subgroup.

As noted above, though the foregoing description describes the inventions particularly in the context of monitoring and/or estimating treatment adherence, the first and second methods S100, S200 can implement similar functionality and techniques to identify patient risk and assess treatment efficacy.

The systems and methods of the embodiments can be embodied and/or implemented at least in part as a machine configured to receive a computer-readable medium storing computer-readable instructions. The instructions can be executed by computer-executable components integrated with the application, applet, host, server, network, website, communication service, communication interface, hardware/firmware/software elements of a patient computer or mobile device, or any suitable combination thereof. Other systems and methods of the embodiments can be embodied and/or implemented at least in part as a machine configured to receive a computer-readable medium storing computer-readable instructions. The instructions can be executed by computer-executable components integrated by computer-executable components integrated with apparatuses and networks of the type described above. The computer-readable medium can be stored on any suitable computer readable media such as RAMs, ROMs, flash memory, EEPROMs, optical devices (CD or DVD), hard drives, floppy drives, or any suitable device. The computer-executable component can be a processor, though any suitable dedicated hardware device can (alternatively or additionally) execute the instructions.

As a person skilled in the art will recognize from the previous detailed description and from the figures and claims, modifications and changes can be made to the embodiments of the invention without departing from the scope of this invention as defined in the following claims.

We claim:

1. A method for improving health risk determination for a patient, the method comprising:
    accessing a log of use corresponding to a communication application for a mobile computing device associated with the patient;
    collecting location data corresponding to a location sensor of the mobile computing device;
    collecting motion data corresponding to a motion sensor of the mobile computing device;
    selecting a patient subgroup for the patient from a first subgroup and a second subgroup based on the location data and the motion data, wherein the first subgroup is selected in response to the location data and the motion data indicating a first mobility behavior shared by the first subgroup, wherein the second subgroup is selected in response to the location data and the motion data indicating a second mobility behavior shared by the second subgroup, wherein the selection of the patient subgroup is operable to improve data storage, data retrieval, and the health risk determination;
    retrieving a health risk model associated with the selected patient subgroup, the health risk model defining a correlation between a risk of change in a medical symptom and communication behavior for patients within the subgroup;
    determining a patient risk of change in the medical symptom for the patient based on the log of use and the health risk model; and
    facilitating provision of a health-related intervention for improving a health outcome of the patient, based on the patient risk of change.

2. The method of claim 1, wherein the method further comprises automatically storing the location data, the motion data, and communication data from the log of use in association with the patient subgroup selected from the first and the second subgroups.

3. The method of claim 2, further comprising anonymizing the location data, the motion data, and the communication data prior to automatically storing the location data, the motion data, and the communication data.

4. The method of claim 1, wherein the first mobility behavior comprises a low level of patient physical activity, wherein the first subgroup is selected in response to the location data and the motion data indicating the low level of patient physical activity, wherein the second mobility behavior comprises a high level of patient physical activity, and wherein the second subgroup is selected in response to the location data and the motion data indicating the high level of patient physical activity.

5. The method of claim 1, wherein the first mobility behavior comprises a total patient movement below a threshold, wherein the first subgroup is selected in response to the location data and the motion data indicating movement of the patient being below the threshold, wherein the second mobility behavior comprises a total patient movement above the threshold, wherein the second subgroup is selected in response to the location data and the motion data indicating the movement of the patient being above the threshold.

6. The method of claim 1, wherein determining the patient risk of change in the medical symptom comprises determining the patient risk of change in the medical symptom based on the location data, the motion data, the log of use, and the health risk model.

7. The method of claim 6,
wherein the health risk model defines a correlation between a sleep-related condition and the communication behavior for the patients within the subgroup, and
wherein determining the patient risk of change in the medical symptom comprises predicting a medical diagnosis of the sleep-related condition based on the location data, the motion data, the log of use, and the health risk model.

8. The method of claim 1, further comprising:
in response to the patient risk of change in the medical symptom exceeding a threshold risk, facilitating a digital communication between a care provider and the patient; and
updating the patient risk of change in the medical symptom for the patient based on the digital communication.

9. A method for improving health status determination for a first patient, the method comprising:
accessing a log of use corresponding to a communication application for a first mobile computing device associated with the first patient;
collecting first mobility data corresponding to a first mobility sensor of the first mobile computing device;
selecting a patient subgroup for the first patient from a first subgroup and a second subgroup based on the first mobility data, wherein the first subgroup is selected in response to the first mobility data indicating a first mobility behavior associated with the first subgroup, wherein the second subgroup is selected in response to the first mobility data indicating a second mobility behavior associated with the second subgroup, wherein the selection of the patient subgroup is operable to improve data storage, data retrieval, and the health status determination;
retrieving a health risk model associated with the selected patient subgroup, the health risk model defining a correlation between health status and communication behavior for patients associated with the subgroup;
determining a patient health status for the first patient based on the log of use and the health risk model; and
facilitating provision of a health-related intervention for improving the patient health status for the first patient, based on the patient health status.

10. The method of claim 9, wherein selection of the patient subgroup is operable to improve data storage and data retrieval associated with health status determination, and wherein the method further comprises, at a remote computing system communicable with the first mobile computing device and a second mobile computing device associated with a second patient:
automatically storing the first mobility data in association with the selected patient subgroup;
selecting the patient subgroup for the second patient from the first subgroup and the second subgroup based on second mobility data corresponding to a second mobility sensor of the second mobile computing device; and
automatically storing the second mobility data in association with the selected patient subgroup.

11. The method of claim 9, wherein collecting the first mobility data corresponding to the first mobility sensor comprises collecting GPS satellite data corresponding to a GPS receiver of the first mobile computing device comprising the GPS receiver, a microprocessor, a display, and a wireless communication module, wherein selecting the patient subgroup comprises:
wirelessly receiving the GPS satellite data at a remote server from the first mobile computing device, wherein the remote server comprises a central processing unit (CPU);
calculating, by the CPU of the remote server, a location feature based on the GPS satellite data, wherein the location feature is operable to improve health status determination; and
selecting the patient subgroup for the first patient from the first subgroup and the second subgroup based on the location feature.

12. The method of claim 9, wherein collecting the first mobility data corresponding to the first mobility sensor comprises collecting motion data corresponding to a set of inertial sensors mounted at the first mobile computing device, and wherein selecting the patient subgroup comprises:
determining an orientation of the first mobile computing device based on the motion data; and
selecting the patient subgroup for the first patient from the first subgroup and the second subgroup based on the orientation of the first mobile computing device.

13. The method of claim 9, wherein accessing the log of use comprises extracting a voice communication feature for the first patient from the log of use, and wherein determining the patient health status for the first patient comprises determining the patient health status based on the voice communication feature and the health risk model.

14. The method of claim 13, further comprising: collecting a phone usage feature indicating phone usage behavior of the first patient associated with the first mobile computing device, wherein determining the patient health status for the first patient comprises determining the patient health status based on the phone usage feature, the voice communication feature, and the health risk model.

15. The method of claim 9, wherein the health risk model defines a correlation between a mental health status and the communication behavior for patients associated with the subgroup, and wherein determining the patient health status for the first patient comprises determining a patient mental health status for the first patient based on the first mobility data, the log of use, and the health risk model.

16. The method of claim 15, further comprising determining a treatment regimen for the patient mental health status of the first patient based on the first mobility data and the log of use, wherein the treatment regimen is operable to improve the patient mental health status of the first patient.

17. The method of claim 16, wherein the treatment regimen comprises a medication regimen associated with at least one of medication type and medication dosage, and wherein determining the treatment regimen comprises determining the at least one of the medication type and the medication dosage for the first patient based on the first mobility data and the log of use.

18. The method of claim 15, wherein the mental health status comprises at least one of: a depression disorder, an anxiety disorder, a bipolar disorder, and a psychotic disorder.

19. The method of claim 9, wherein the log of use indicates a communication behavior associated with a communication between the first patient and a care provider, and wherein selecting the patient subgroup comprises selecting the patient subgroup based on the communication behavior and the first mobility data.

20. The method of claim 9, wherein determining the patient health status comprises predicting a risk of increased symptom severity for symptoms associated with a disease based on the log of use and the health risk model.

21. The method of claim 20, further comprising transmitting a notification to a care provider in response to the risk of increased symptom severity exceeding a threshold risk associated with the disease.

22. The method of claim 21, wherein the health risk model defines a correlation between a change in the communication behavior and risk of hospital admission within a specified period of time, and wherein determining the patient health status comprises predicting a risk of hospital admission for the first patient within the specified period of time, and wherein transmitting the notification to the care provider comprises transmitting the risk of hospital admission within the specified period of time to a hospital associated with the first patient.

23. The method of claim 9, further comprising:
identifying a relationship between changes in communication behavior and changes in symptom severity for patients within the patient subgroup; and
generating the health risk model based on the relationship.

24. The method of claim 9, wherein determining the patient health status comprises:
identifying a change in a composite function associated with stress and productivity of the patient based on the log of use; and
determining the patient health status based on the health risk model and the change in the composite function associated with stress and productivity.

* * * * *